US008882691B2

(12) United States Patent
Ogawa

(10) Patent No.: US 8,882,691 B2
(45) Date of Patent: Nov. 11, 2014

(54) NAIL CORRECTING DEVICE AND MEDICAL SET FOR NAIL CORRECTION

(75) Inventor: Akira Ogawa, Kasukabe (JP)

(73) Assignee: Actment Co., Ltd, Kasukabe-Shi (JP)

( * ) Notice: Subject to any disclaimer, the term of this patent is extended or adjusted under 35 U.S.C. 154(b) by 145 days.

(21) Appl. No.: 13/361,178

(22) Filed: Jan. 30, 2012

(65) Prior Publication Data

US 2012/0197172 A1 Aug. 2, 2012

(30) Foreign Application Priority Data

Jan. 31, 2011 (JP) ................................ 2011-017926
Dec. 6, 2011 (JP) ................................ 2011-266866

(51) Int. Cl.

*A61F 5/00* (2006.01)
*A61K 31/00* (2006.01)
*A61F 5/11* (2006.01)

(52) U.S. Cl.

CPC .. *A61F 5/11* (2013.01); *A61K 31/00* (2013.01)
USPC .............................................. 602/31; 602/30

(58) Field of Classification Search

USPC ............ 602/30–31, 23, 11, 22; 128/893, 846, 128/892; 424/61, 443, 448, 404, 408, 400; 132/73, 73.5, 76.2

See application file for complete search history.

(56) References Cited

U.S. PATENT DOCUMENTS 3,173,416 A * 3/1965 Rederich ........................ 602/31
3,464,408 A 9/1969 Hamlin
4,961,732 A * 10/1990 Stienstra ...................... 604/293
6,095,995 A * 8/2000 Machida ........................ 602/30
7,008,391 B2 * 3/2006 Machida ........................ 602/30
2009/0078277 A1 * 3/2009 Uemura ...................... 132/73.5
2010/0160845 A1 6/2010 Yoshikawa

FOREIGN PATENT DOCUMENTS

EP 1 477 144 A2 11/2004
EP 1 985 266 A1 10/2008
GB 928885 6/1963
GB 2 147 211 A 5/1985
JP A-08-215227 8/1996
JP A-09-253110 9/1997
JP A-09-253111 9/1997
JP U-3091516 2/2003
JP A-2004-329646 11/2004
JP A-2007-185203 7/2007

OTHER PUBLICATIONS

Mar. 13, 2012 Office Action issued in Japanese Patent Application No. 2011-266866 (with translation).
Extended European Search Report issued in European Patent Application No. 12152981.2 dated May 18, 2012.

* cited by examiner

*Primary Examiner* — Ophelia A Hawthorne
(74) *Attorney, Agent, or Firm* — Oliff PLC

(57) ABSTRACT

A device includes: a cylindrical body formed of an elastic material; and a slit formed along a longitudinal direction of the cylindrical body from one end to an opposite end of the cylindrical body, a distal end of a nail being inserted to be held in the slit. The cylindrical body includes: plural pairs of holding teeth plurally divided in the longitudinal direction of the cylindrical body by dividing grooves formed from the slit along a circumferential direction of the cylindrical body such that the holding teeth of each pair are opposed to each other across the slit to hold the distal end of the nail; and coupling pieces configured to couple adjacent ones of the holding teeth on an opposite side of the slit.

13 Claims, 28 Drawing Sheets

| GAP (mm) | UNMATING FORCE (N) | |
|---|---|---|
| | W/ TOPCOAT | W/O TOPCOAT |
| 0.7 | 0.83 | 2.94 |
| 0.8 | 0.73 | 2.69 |
| 0.9 | 0.54 | 1.23 |
| 1 | 0.54 | 1.76 |
| 1.1 | 0.29 | 1.37 |

CIRCULAR BENDING TEST

FIG. 28

RESULTS OF CIRCULAR BENDING TEST

| | BENDING ANGLE | $\phi$ 6.5mm(PLUG) | DEFORMATION (LESS RESILIENCE) |
|---|---|---|---|
| 1 | 90 DEGREES | (2.45N) | NONE |
| 2 | 120 DEGREES | (2.50N) | NONE |
| 3 | 150 DEGREES | (2.40N) | SLIGHTLY |
| 4 | 180 DEGREES | (2.50N) | A BIT |

NAIL CORRECTING DEVICE AND MEDICAL SET FOR NAIL CORRECTION

The entire disclosure of Japanese Patent Applications No. 2011-017926 filed Jan. 31, 2011 and No. 2011-266866 filed Dec. 6, 2011 is expressly incorporated by reference herein.

BACKGROUND OF THE INVENTION

1. Field of the Invention

The present invention relates to a nail correcting device and a medical set for nail correction for correcting a deformed nail such as an ingrown nail and a pincer nail.

2. Description of Related Art

An ingrown nail causes inflammation because the side edges of the ingrown nail are curved inward to press or dig into a soft tissue (e.g., a toe skin) with pain, which may result in symptoms such as granulation and pyogenesis. It should be noted that the ingrown nails of many patients are also considered as pincer nails, the side edges of which curl inward.

There have been proposed typical correcting devices for correcting deformed nails such as a pincer nail and an ingrown nail.

For instance, there have been proposed correcting devices according to which the shape of a normal nail is beforehand memorized in a plate-like body or a tape-like body formed of a shape-memory alloy or a shape-memory resin at a predetermined temperature, and the plate-like body or the tape-like body is attached to a deformed nail with an adhesive (see Patent Literature 1: JP-A-8-215227, Patent Literature 2: JP-A-9-253110 and Patent Literature 3: JP-A-9-253111).

However, since the above typical correcting devices require a strong adhesive for attaching the plate-like body or the like to a nail, it takes a long time before the adhesive dries up, and, further, the plate-like body or the like has to be pressed down with tweezers or the like until the adhesive dries up. Thus, the typical correcting devices are quite tricky to use. Further, when the adhesive adheres not to a nail but to a skin or the like, the skin is irritated and suffers from an injury such as abrasion.

In view of the above, the inventor has proposed an ingrown nail correcting device capable of solving the above problems (see Patent Literature 4: JP-A-2007-185203). This ingrown nail correcting device includes a plate-like body formed of an elastic material and a plurality of holding units provided to the plate-like body at intervals to hold the distal end of a nail. Each of the holding units includes an upper holder and a lower holder.

When the ingrown nail correcting device is in use, the distal end of a nail is inserted in the holding units of the correcting device so that the distal end of the nail is held between the upper holders and the lower holders of the holding units. In this manner, a lifting force constantly acts on both side edges of the nail in an upward direction, so that a correcting effect on the deformed nail can be provided.

However, the ingrown nail correcting device previously proposed by the inventor has the following problems (i) to (iii).

(i) Since the correcting device employs the plate-like body and thus the distal end of a nail is merely held by the holding units, an accidental detachment of the correcting device from the nail may easily happen because of a weak nail-holding force thereof.

(ii) Since an accidental detachment of the correcting device may easily happen, the correcting device needs to be held with a tape or fixed with an adhesive, which may require a tricky operation. In particular, the use of such a correcting device may be dangerous for a patient with inflammation.

(iii) The correcting device may be inserted between a nail and the finger when the nail is not sufficiently grown. In this case, when the correcting device contacts with an object, the lower holders of the holding units are further inserted between the nail and the finger, so that the patient may feel a strong pain.

SUMMARY OF THE INVENTION

Accordingly, an object of the invention is to provide a nail correcting device and a medical set for nail correction that are capable of: being easily attached to and detached from even an insufficiently grown deformed nail with less possibility of an accidental detachment from the nail; providing an appropriate and uniform correcting force; and easing the pain of a patient in use.

According to an aspect of the invention, a nail correcting device includes: a cylindrical body being formed of an elastic material; and a slit being formed in a longitudinal direction of the cylindrical body from one end to an opposite end of the cylindrical body, a distal end of a nail being inserted to be held in the slit.

The cross-sectional shape of the cylindrical body may be any one of a circle, a flattened circle, and a polygon. The cylindrical body may be formed of any material as long as the material has elasticity. For instance, an elastic body having superelasticity or shape-memory properties may be usable. In addition, any one of elastic materials such as stainless steel, titanium alloy, copper alloy and irons and an elastic material such as plastics may also be usable.

With the above arrangement, when the distal end of a nail is inserted in the slit formed in the longitudinal direction from one end to the opposite end of the cylindrical body, the slit holds the distal end of the nail. The nail correcting device can thus be easily attached to the nail. Further, the nail correcting device can be easily detached from the nail merely by pulling the nail away from the slit. In addition, since the cylindrical body is made of an elastic material, the nail correcting device is applicable to any type of fingernail irrespective of the shape or the thickness thereof.

Since the distal end of the nail is held in the slit formed along the longitudinal direction of the cylindrical body, an accidental detachment of the nail correcting device from the nail is unlikely to happen. Further, the nail correcting device can provide an appropriate and uniform correcting force to the entire deformed nail because the correcting force uniformly acts on the nail over the entire length of the slit. Thus, a correcting effect on the deformed nail can be achieved.

Even when the nail correcting device attached to the deformed nail accidentally contacts with an object, a further insertion of the nail correcting device between the nail and the finger is avoidable because the nail correcting device is in a cylindrical shape. Thus, the patient can feel less pain.

It should be noted that the "deformed nail" herein includes a pincer nail, an ingrown nail, and a nearly deformed nail likely to become any one of them.

In the above aspect, it is preferable that the cylindrical body includes: plural pairs of holding teeth being plurally divided in the longitudinal direction of the cylindrical body by dividing grooves formed from the slit along a circumferential direction of the cylindrical body such that the holding teeth of each pair are opposed to each other across the slit to hold the distal end of the nail; and coupling pieces being configured to couple adjacent ones of the holding teeth on an opposite side of the slit.

In the above arrangement, the cylindrical body is provided with the plural pairs of holding teeth being plurally divided in the longitudinal direction of the cylindrical body by the dividing grooves formed from the slit along the circumferential direction of the cylindrical body. The holding teeth of each pair are opposed to each other across the slit to hold the distal end of the nail at the front and back surfaces of the nail. When the distal end of the nail is inserted in the slit formed in the cylindrical body, the intervals between the holding teeth are adjusted depending on the curvature of the nail. Specifically, the intervals between the holding teeth located on the front side of the nail are increased in the longitudinal direction while the intervals between the holding teeth located on the back side (inner side) of the nail are reduced in the longitudinal direction. Thus, the nail correcting device is deformable along the curved surface of the nail to fit with the nail so as to provide a uniform correcting force over the entire width of the nail. As a result, the nail correcting device is less accidentally detachable and a continuous correction with an appropriate force is possible.

In the above aspect, it is preferable that each pair of holding teeth includes: a belt-like frame being formed with a substantially constant width along an outer profile of the holding teeth; and a space being surrounded by the belt-like frame.

With the above arrangement, since the holding teeth define the space surrounded by the belt-like frame formed in conformity with the outer profile, the belt-like frame is easily deformable due to the space. Thus, the widths of the holding teeth located on the front side of the nail can be further increased in the longitudinal direction while the widths of the holding teeth located on the back side (inner side) of the nail can be further reduced in the longitudinal direction, so that the nail correcting device is applicable to a deformed nail with a large curve. In addition, by enlarging or narrowing the spaces interposed between the coupling pieces in the longitudinal direction of the cylindrical body, the dividing grooves are deformed and the slit of the cylindrical body is curved in a width direction thereof. Thus, the nail correcting device can be deformed in accordance with the curve of the nail to fit with the nail.

In the above aspect, it is preferable that an end of each of the holding teeth is formed in an arc.

The "arc" herein includes a shape provided by rounding the corners of a rectangular shape.

With the above arrangement, since a portion in contact with the nail is in an arc, the portion is unlikely to scratch the nail. In particular, since each of the ends of the holding teeth is in an arc, the nail correcting device can be smoothly attached or detached by sliding the holding teeth without scratching the nail and damaging the nail with the edges of the holding teeth.

In the above aspect, it is preferable that the nail correcting device is formed of a material exhibiting any one of a superelasticity effect and a shape-memory effect.

When the nail correcting device is formed of a material exhibiting a superelasticity effect, the nail correcting device can have a large elastic limit (have a plateau area). Thus, even when the nail correcting device is significantly deformed, a stress is not so increased and thus the nail does not suffer from a large load. Thus, the nail correcting device is applicable to a significantly deformed nail to ease the pain of a patient accompanied by nail correction.

The nail correcting device may be formed of a material having a shape-memory effect whose Af point (shape-recovery temperature) is a temperature slightly higher than the body temperature (e.g., 38 degrees C. or higher). In this case, although the nail correcting device usually exhibits a small correcting force, when the nail is softened during bath time or the like, the nail correcting device exhibits a large correcting force because the elastic modulus thereof approximately triples. For instance, when a strong pain from a deformed nail disturbs an ordinary life, the foot or the nail may be heated with hot water or a dryer to heat the correcting device to the Af point or higher. As a result, the correcting force can be increased, so that the nail is prevented from digging, thereby easing the pain in the foot.

In the above aspect, it is preferable that the nail correcting device is coated or impregnated with a medical agent.

The medical agent herein includes a therapeutic agent for fungal infection, an antibacterial agent capable of killing or deactivating germs for infection treatment, and the like. Examples of these agents are croconazole hydrochloride, butenafine hydrochloride, siccanin and tolnaftate.

With the above arrangement, since the nail correcting device is impregnated or coated with the medical agent, the medical agent can be applied to a soft tissue of the foot (e.g., a toe skin) for prophylaxis or treatment of fungal infection or the like.

In the above aspect, it is preferable that a medical capsule is housed inside the cylindrical body, the medical capsule being configured to contain a medical agent and gradually eject the contained medical agent.

With the above arrangement, the above treatment effect can be achieved simply by setting the medical capsule in the cylindrical body.

According to another aspect of the invention, a medical set for nail correction, includes: the above nail correcting device; and an adhesive being used to fix the nail correcting device on a nail.

When the clearance of the slit formed in the cylindrical body is small, it is difficult to attach the nail correcting device to a nail. On the other hand, when the clearance of the slit is large, an accidental detachment of the nail correcting device from a nail is likely to happen. Accordingly, it is desired that the nail correcting device should solve such contradictory problems. However, nail thickness differs among people and among fingers to which the device is to be attached. While the nail of a thumb is thick, those of an index finger, a middle finger, ring finger and little finger are thin.

With the above arrangement, since the medical set includes the adhesive usable to fix the nail correcting device to a nail, after the nail correcting device is attached to the distal end of the nail, the adhesive can be applied thereon to fix the nail correcting device to the nail. Thus, even when the nail correcting device is formed to be easily attachable to the nail, an accidental detachment of the nail correcting device from the nail is unlikely to happen.

For the adhesive, a topcoat (an aqueous acrylic) and a gel nail polish (a gel resin curable by ultraviolet irradiation) are usable.

In the above aspect, it is preferable that the adhesive is impregnated with a medical agent.

With the above arrangement, the medical agent, such as a therapeutic agent for fugal infection or an antibacterial agent, contained in the adhesive can be applied to a soft tissue of the foot (e.g., a toe skin) for prophylaxis or treatment of fungal infection or the like.

BRIEF DESCRIPTION OF THE DRAWINGS

FIG. 26 shows a difference in an unmating force depending on whether or not the nail correcting device according to the first exemplary embodiment is coated with a topcoat.

FIG. 28 shows results of the above test.

DETAILED DESCRIPTION OF PREFERRED EMBODIMENT

First Exemplary Embodiment (See FIGS. 1 to 7)

Figure 1:
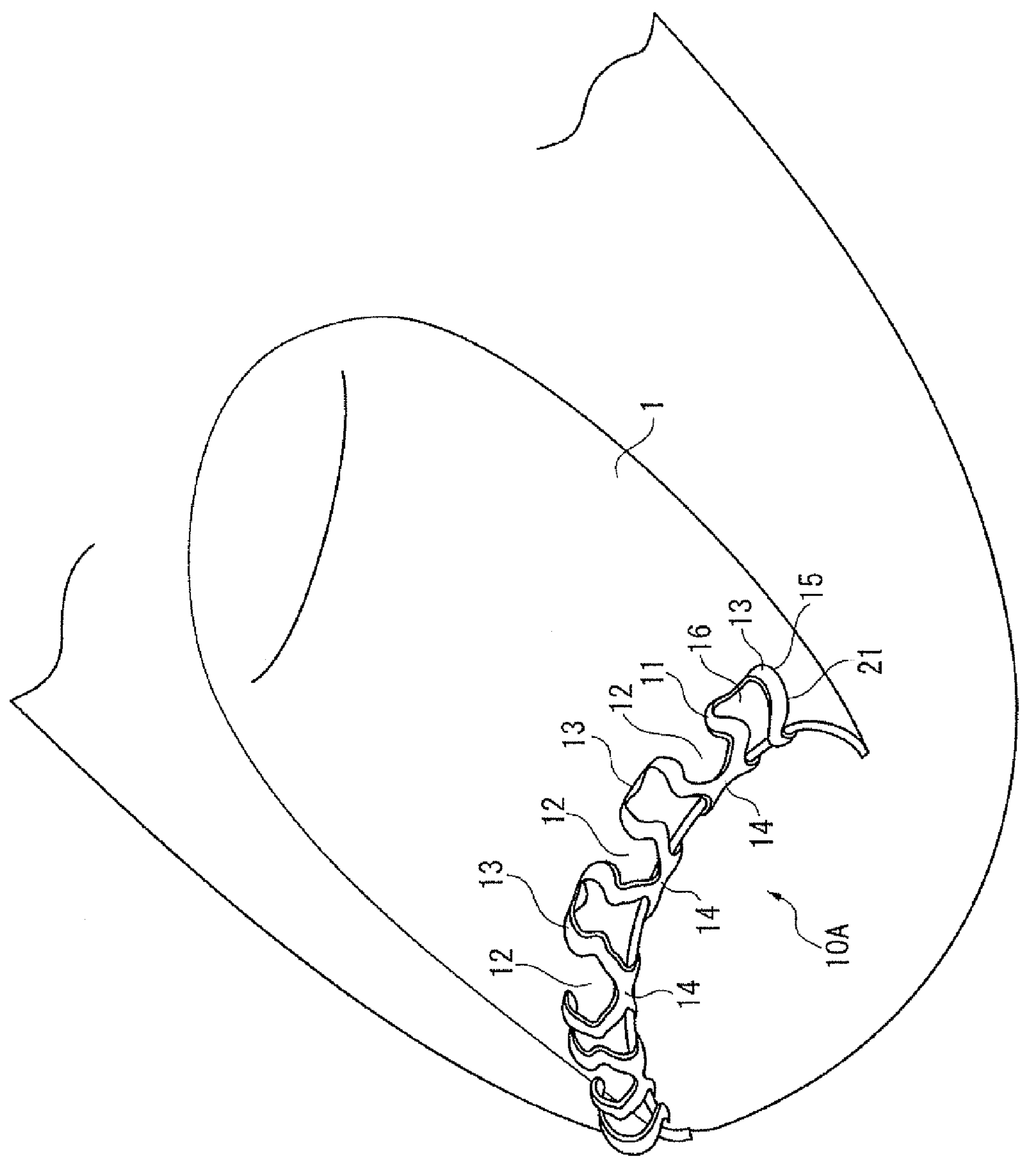
FIG. 1 is a perspective view showing a nail correcting device according to a first exemplary embodiment of the invention attached to a nail.
Figure 2:
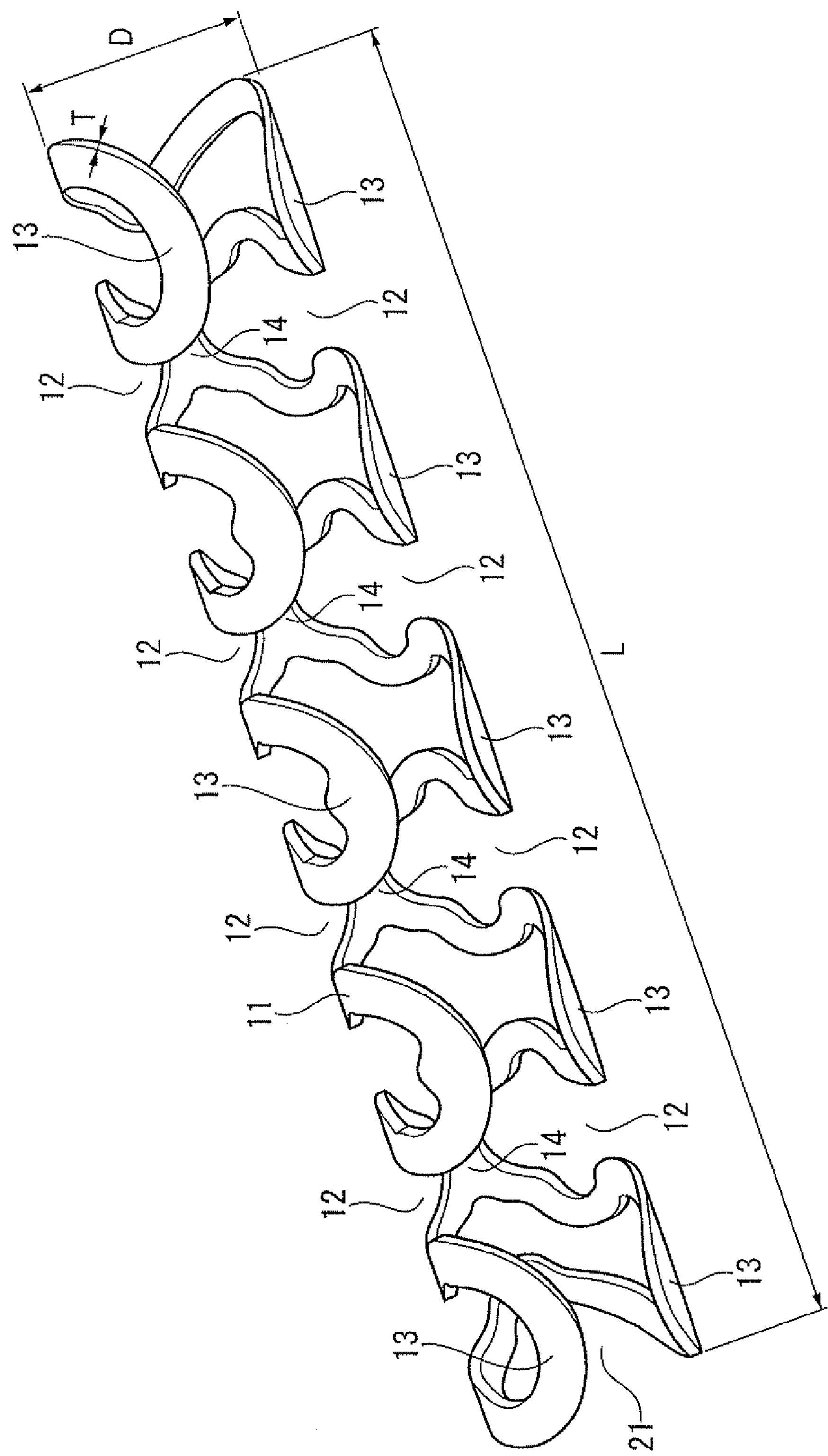
FIG. 2 is a perspective view showing the nail correcting device according to the first exemplary embodiment.
Figure 3:
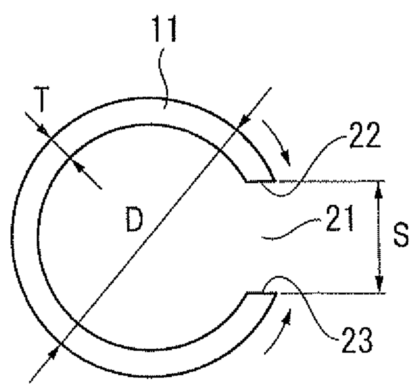
FIG. 3 is a side view showing the nail correcting device according to the first exemplary embodiment.

As shown in FIGS. 1 to 3, a nail correcting device 10A according to a first exemplary embodiment is configured to correct a nail 1 (i.e., an ingrown nail, a pincer nail or the like), and is attachable to the nail 1 for correction. The nail correcting device 10A includes a cylindrical body 11, and a slit 21 being formed in a longitudinal direction of the cylindrical body 11 from one end to the opposite end of the cylindrical body 11 and in which the distal end of the nail 1 is inserted to be held. The entirety of the nail correcting device 10A is formed of a superelastic material having elasticity and has a C-shaped cross section.

A longitudinal dimension L of the cylindrical body 11 is determined depending on the width of the nail 1 to be corrected, and falls within a range, for instance, approximately from 5 mm to 20 mm. An outer diameter D of the cylindrical body 11 is determined depending on the curvature of the nail 1 to be corrected, and falls within a range, for instance, approximately from 1.2 mm to 4.0 mm. A thickness T of the cylindrical body 11 is determined with reference to a relationship with a material used to form the nail correcting device 10A, and falls within a range, for instance, approximately from 0.02 mm to 0.5 mm.

Figure 4:
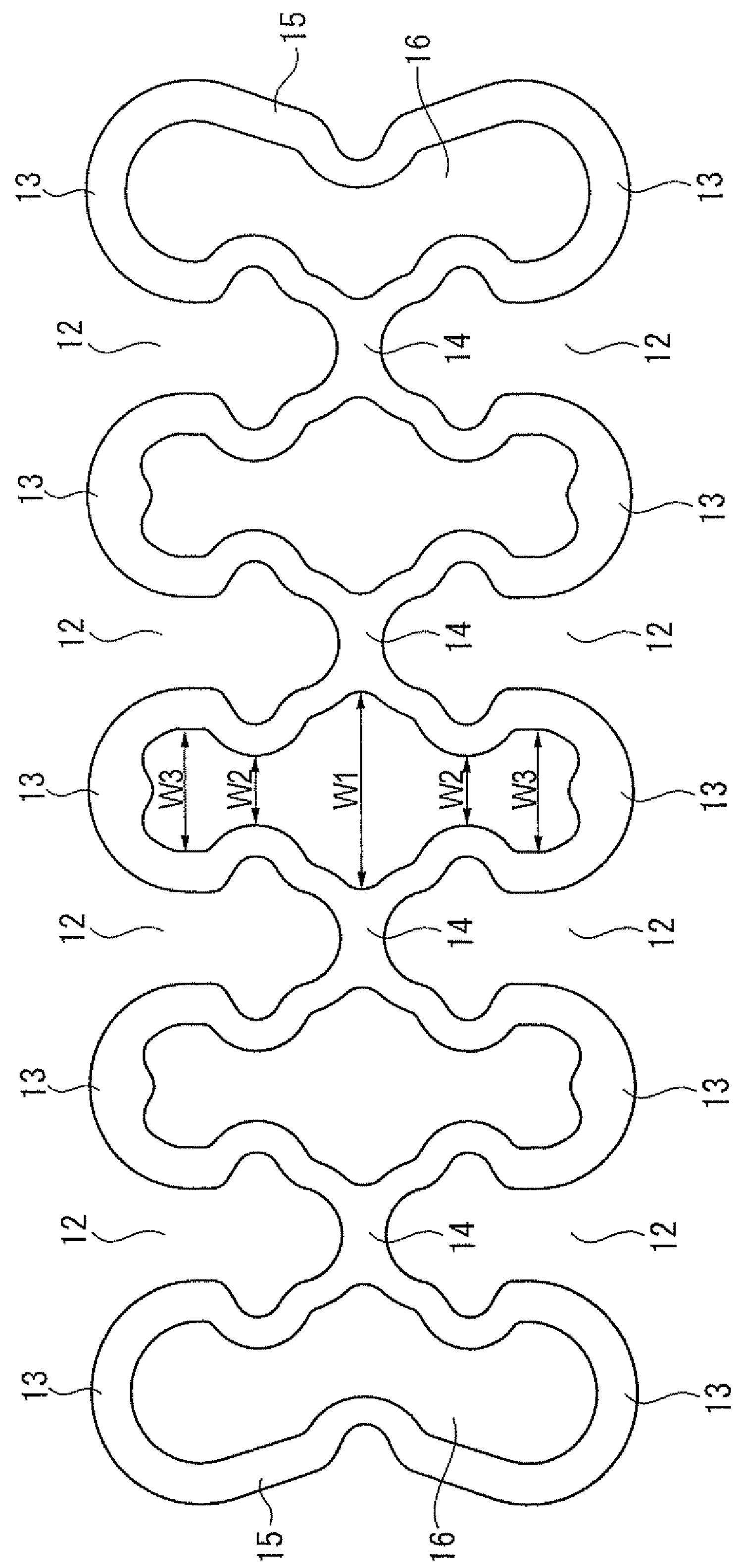
FIG. 4 is a developed view of the nail correcting device according to the first exemplary embodiment.

As shown in a developed view of FIG. 4 in detail, plural pairs (five pairs) of holding teeth 13 and coupling pieces 14 are formed in an outer circumferential surface of the cylindrical body 11. The plural pairs of holding teeth 13 are plurally divided in the longitudinal direction of the cylindrical body 11 by dividing grooves 12 formed from the slit 21 along a circumferential direction of the cylindrical body 11. The holding teeth 13 of each pair are opposed to each other across the slit 21 to hold the distal end of the nail 1. The coupling pieces 14 extend substantially in parallel with the slit 21 on the opposite side of the slit 21 to couple adjacent ones of the holding teeth 13.

Each pair of the holding teeth 13 includes a belt-like frame 15 being formed with a substantially constant width in conformity with an outer profile of the holding teeth 13, and a space 16 being surrounded by the belt-like frame 15. The end of each of the holding teeth 13 is formed in an arc. The belt-like frame 15 of the holding teeth 13 opposed to each other across the slit 21 is shaped such that both sides of the belt-like frame 15 extend inward from both ends of the arc in a mutually approaching direction toward the coupling pieces 14, and then extend in a mutually separating direction to be integrally coupled to the coupling pieces 14. Thus, the space 16 surrounded by the belt-like frame 15 has different widths, namely a width W1 (a dimension in the longitudinal direction of the cylindrical body 11) of a central portion thereof where the coupling pieces 14 are located, a width W2 at a middle portion of each of the holding teeth 13, and a width W3 at an end portion of each of the holding teeth 13. The width W1 is the widest, the width W2 is the narrowest, and the width W3 is not so wide as the width W1 but is wider than the width W2.

The slit 21 is defined by cut surfaces formed by cutting the cylindrical body 11 along the longitudinal direction from one end to the opposite end thereof. The slit 21 is defined by an upper holder 22 (one of the cut surfaces) and a lower holder 23 (the other of the cut surfaces). A clearance dimension S of the slit 21 (an interval between the upper holder 22 and the lower holder 23) is determined in accordance with the thickness or the curve of the nail 1 to be corrected, and falls within a range, for instance, approximately from 0.3 mm to 2.5 mm, usually approximately from 0.5 mm to 1.6 mm.

Method of Manufacturing Nail Correcting Device

The nail correcting device 10A may be manufactured by processing a material in a netlike pattern using a laser processing machine in the same manner as a stent or the like. Additionally, the material may also be processed by an etching process or the like. These processing methods will be described below.

Figure 5:
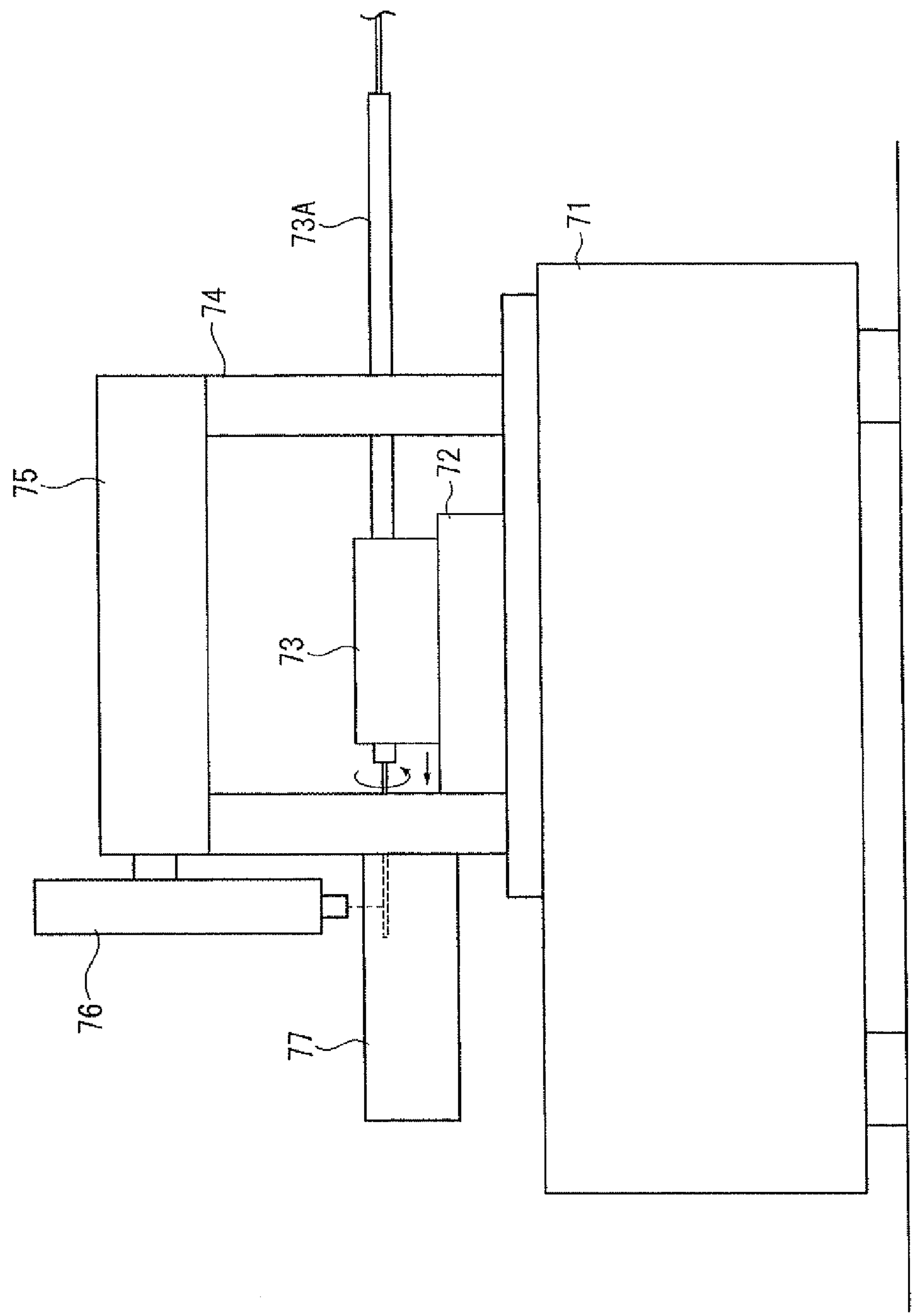
FIG. 5 shows a manufacturing machine (a laser processing machine) for the nail correcting device according to the first exemplary embodiment.

FIG. 5 shows a laser processing machine. The laser processing machine includes: a base 71; a rotary feeding mechanism 73 being mounted on the base 71 via a support block 72, the rotary feeding mechanism 73 including a guide tube 73A that guides a cylindrical material 11A (a cylindrical material provided by forming a slit in a pipe cylindrically formed of a superelastic material, a shape-memory alloy or the like) for the nail correcting device, the rotary feeding mechanism 73 being configured to axially feed the cylindrical material 11A in the guide tube 73A in a rotatable manner; a laser-emitting device 75 being mounted on the base 71 via a support leg 74; a laser processor 76 being configured to direct the optical path of a laser beam emitted from the laser-emitting device 75 downward to irradiate the cylindrical material 11A; and a collecting case 77 in which the nail correcting device processed by the laser processor 76 is collected.

For the processing, the cylindrical material 11A is inserted in the guide tube 73A of the rotary feeding mechanism 73. The cylindrical material 11A inserted in the guide tube 73A is axially fed in a rotatable manner while being processed in a netlike pattern with the laser beam emitted from the laser processor 76, and then is collected in the collecting case 77.

In an actual processing, water is supplied in the cylindrical material 11A. This is because the water in the cylindrical material 11A serves to diffuse the laser beam emitted from the laser processor 76 after the upper side of the cylindrical material 11A is processed with the laser beam, so that the lower side of the cylindrical material 11A is prevented from being processed with the laser beam.

Figure 6:
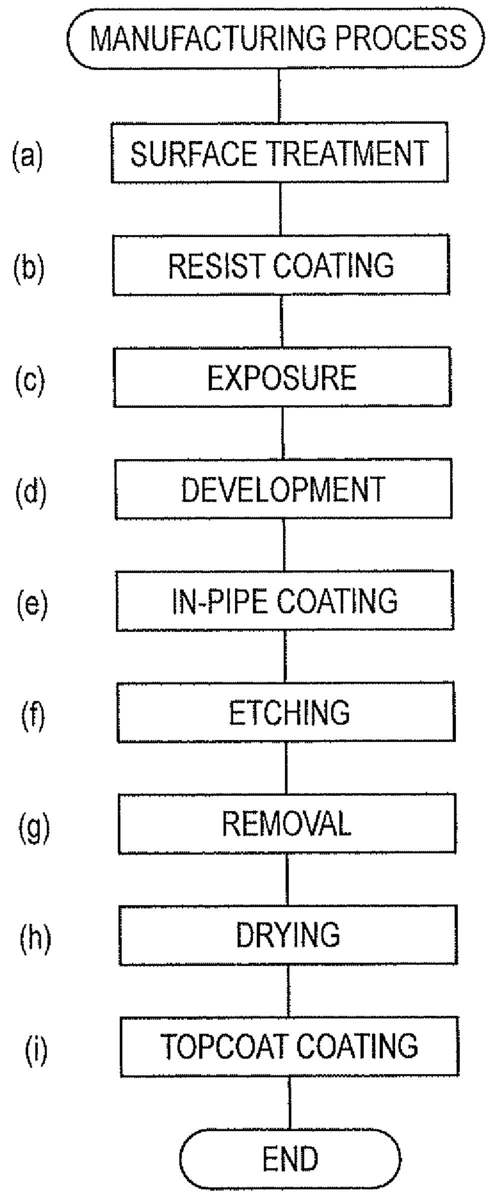
FIG. 6 shows a manufacturing process (etching) for the nail correcting device according to the first exemplary embodiment.

An exemplary etching process will be described below with reference to FIG. 6.

(a) Surface Treatment Step

A cylindrical material provided by forming a slit in a pipe cylindrically formed of a superelastic material, a shape-memory alloy or the like is beforehand prepared. The cylindrical material is degreased, rinsed, neutralized and rinsed.

(b) Resist Coating Step

After the surface treatment step, a surface of the cylindrical material is coated with a resist (a sensitizer).

(c) Exposure Step

Figure 7:
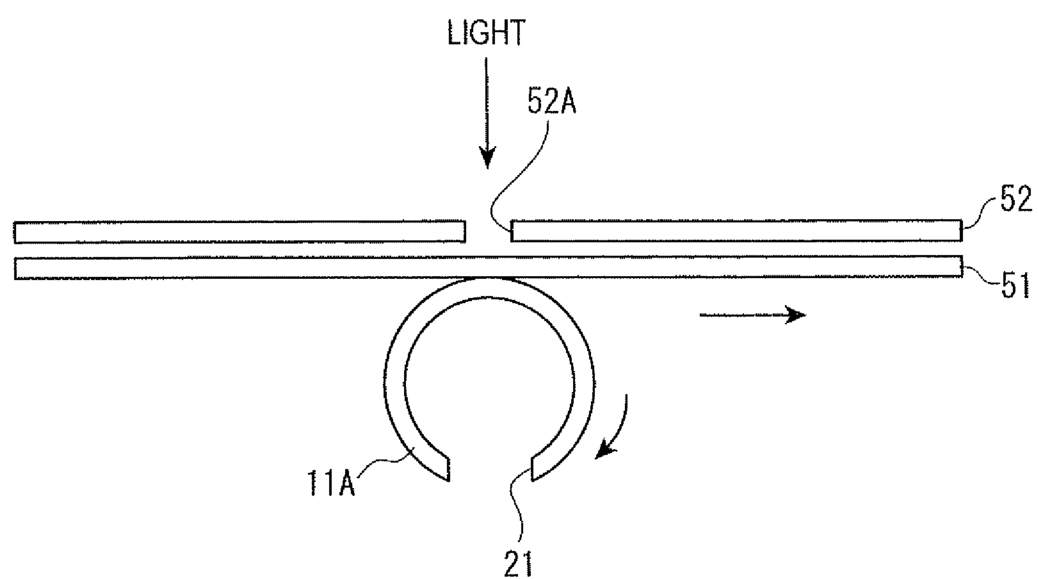
FIG. 7 shows an exposure step in the manufacturing process for the nail correcting device according to the first exemplary embodiment.

For instance, as shown in FIG. 7, a film-attached original plate 51, which is provided by firmly attaching a film on a glass substrate for light shielding except portions corresponding to the holding teeth and the coupling pieces, is kept in contact with the cylindrical material 11A, and a slit-exposure jig 52 is set thereon. In this state, while a light (ultraviolet) is radiated through an exposure window 52A of the slit-exposure jig 52, the cylindrical material 11A is rotated. The film-attached original plate 51 slides during the rotation of the cylindrical material 11A, so that the resist on the outer circumferential surface of the cylindrical material 11A is exposed at the portions corresponding to the holding teeth and the coupling pieces.

(d) Developing Step

After the exposure step, the cylindrical material 11A is immersed in a developer for a predetermined duration of time to remove a residual resist, and then rinsed.

(e) In-Pipe Coasting Step

The inner surface of the cylindrical material is coated with a resist (a sensitizer).

(f) Etching Step

After the in-pipe coating step, the cylindrical material is immersed in an etching solution for a predetermined duration of time to form the dividing grooves, the holding teeth and the coupling piece in the cylindrical material.

(g) Removing Step

A residual resist is removed.

(h) Drying Step

The cylindrical material is dried at a predetermined temperature for a predetermined duration of time.

(i) Topcoat Coating Step

Finally, the cylindrical material is coated with a coating material, i.e., a topcoat (e.g., an aqueous acrylic or a lacquer). In this manner, the nail correcting device 10A is manufactured.

Attachment of Nail Correcting Device

For attaching the nail correcting device 10A, the slit 21 is opened and the distal end of the nail 1 to be corrected is inserted therein (see FIG. 1). When the upper holder 22 and the lower holder 23 defining the slit 21 hold the nail 1, the nail correcting device 10A is attached to the nail 1. In this manner, the nail correcting device 10A can be easily attached to the nail 1.

The cylindrical body 11 includes the plural pairs of holding teeth 13 being plurally divided in the longitudinal direction of the cylindrical body 11 by the dividing grooves 12 formed from the slit 12 along the circumferential direction of the cylindrical body 11, the holding teeth 13 of each pair are opposed to each other across the slit 21 to hold the distal end of the nail 1. When the nail correcting device 10A is attached to the nail 1, the intervals between the holding teeth 13 located on the front side of the nail 1 are increased in the longitudinal direction while the intervals between the holding teeth 13 located on the back side (inner side) of the nail 1 are reduced in the longitudinal direction.

Thus, the nail correcting device 10A can fit with the nail 1 along the curved surface thereof to apply a correcting force over the entire width of the nail, so that a continuous correction with an appropriate force is possible.

Additionally, since the holding teeth 13 of each pair define the space 16 surrounded by the belt-like frame 15 formed in conformity with the outer profile, the belt-like frame 15 is easily deformable due to the space 16. Thus, the widths of the holding teeth 13 located on the front side of the nail 1 can be further increased in the longitudinal direction while the widths of the holding teeth 13 located on the back side (inner side) of the nail 1 can be further reduced in the longitudinal direction, so that the nail correcting device 10A is applicable to the nail 1 even when the nail 1 has a large curve.

By enlarging or narrowing the spaces 16 interposed between the coupling pieces 14, the dividing grooves 12 are deformed and the slit 21 of the cylindrical body 11 is curved along a width direction thereof, so that the nail correcting device 10A can be curved in accordance with the shape of the distal end of the nail to fit with the nail.

The end of each of the holding teeth 13 is formed in an arc. Thus, the nail correcting device 10A is unlikely to scratch the nail 1, so that the nail correcting device 10A can be smoothly attached or detached with less damage to the nail 1.

Second Exemplary Embodiment (See FIGS. 8 to 11)

Figure 8:
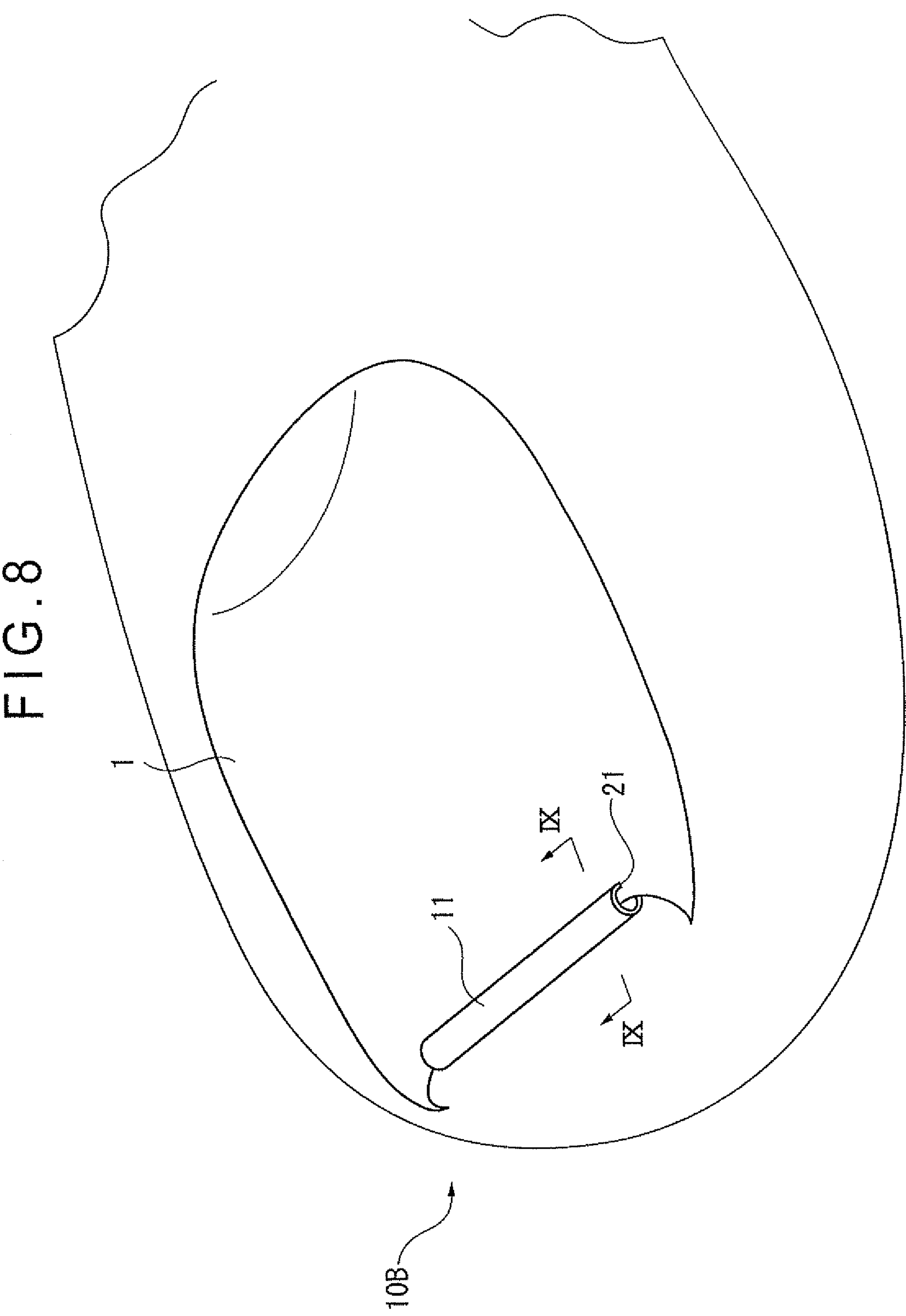
FIG. 8 is a perspective view showing a nail correcting device according to a second exemplary embodiment of the invention attached to a nail.
Figure 9:
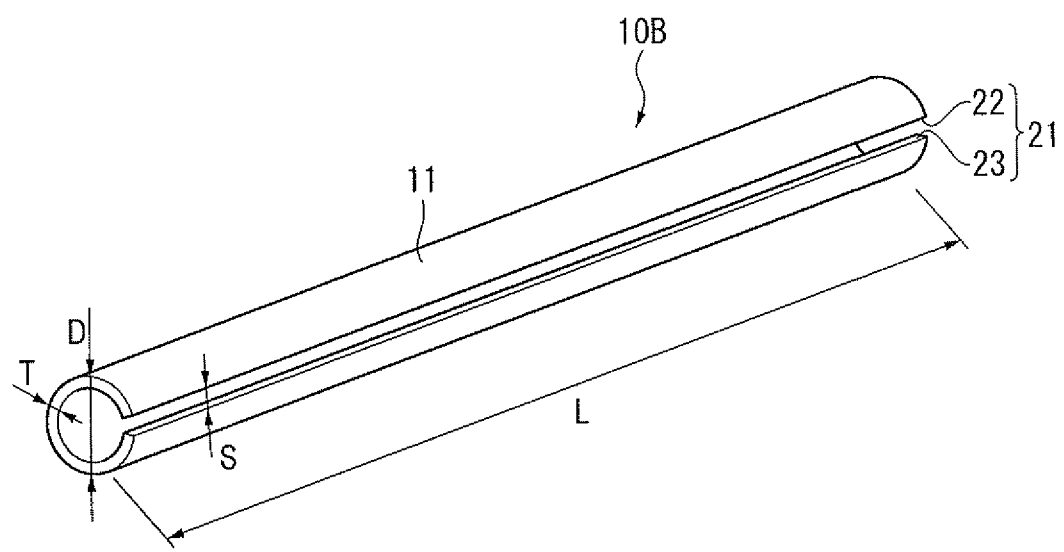
FIG. 9 is a perspective view showing the nail correcting device according to the second exemplary embodiment.
Figure 10:
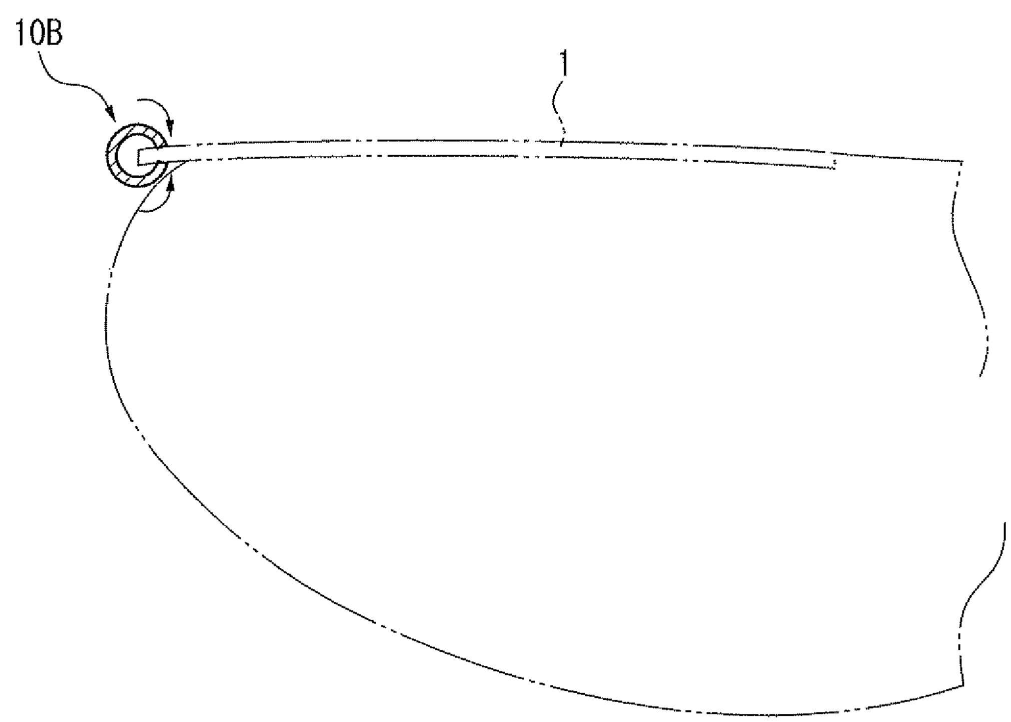
FIG. 10 is a sectional view showing a cross section of the nail correcting device according to the second exemplary embodiment.

As shown in FIGS. 8 to 10, a nail correcting device 10B according to a second exemplary embodiment includes the cylindrical body 11, and the slit 21 being formed in the longitudinal direction of the cylindrical body 11 from one end to the opposite end of the cylindrical body 11 and in which the distal end of the nail 1 is inserted to be held. The entirety of the nail correcting device 10B is formed of a superelastic material having elasticity and has a C-shaped cross section. In other words, the nail correcting device 10B is different from the nail correcting device 10A according to the first exemplary embodiment in that the cylindrical body 11 of the nail correcting device 10B does not include the dividing grooves 12, the plural pairs (five pairs) of holding teeth 13, the coupling pieces 14, and the like.

As compared with the nail correcting device 10A according to the first exemplary embodiment, the nail correcting device 10B according to the second exemplary embodiment can be manufactured in a relatively facilitated manner with less cost because it is not necessary to form the dividing grooves 12, the holding teeth 13, the coupling pieces 14 and the like in the cylindrical body 11.

Figure 11:
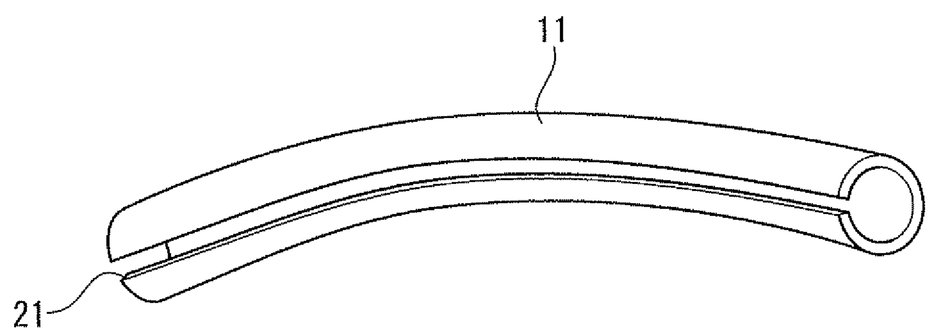
FIG. 11 is a perspective view showing a modification of the nail correcting device according to the second exemplary embodiment.

As shown in FIG. 11, the nail correcting device 10B may be curved in a clearance direction of the slit 21 along the longitudinal direction of the cylindrical body 11 in use in accordance with the shape or curl. In this manner, since the cylindrical body 11 is curved, the correcting force to the nail 1 can be adjusted. For instance, when the nail correcting device 10B is curved at a curvature close to the curvature of the nail 1, the correcting force can be reduced.

Figure 12:
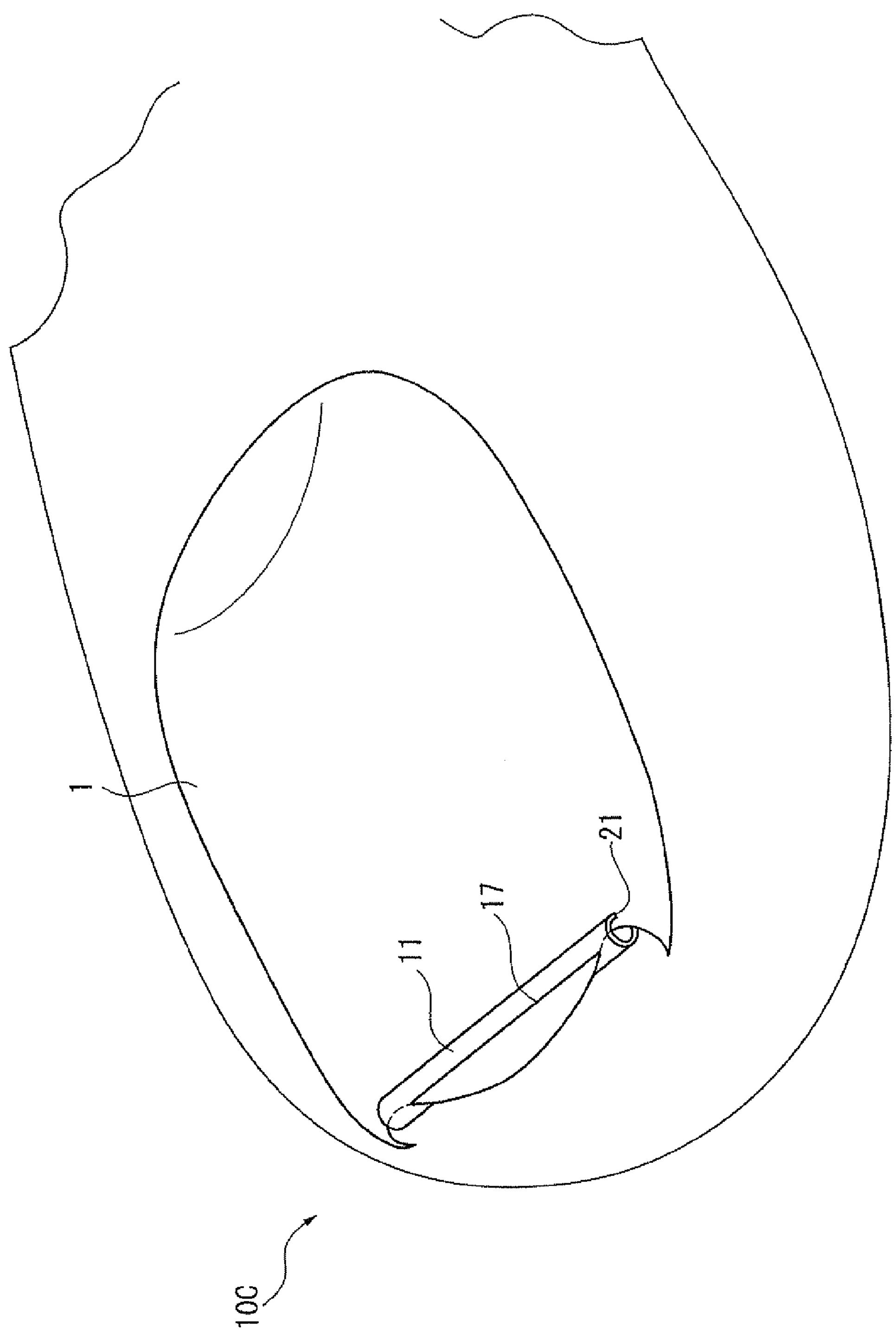
FIG. 12 is a perspective view showing a nail correcting device according to a third exemplary embodiment of the invention attached to a nail.
Figure 13:
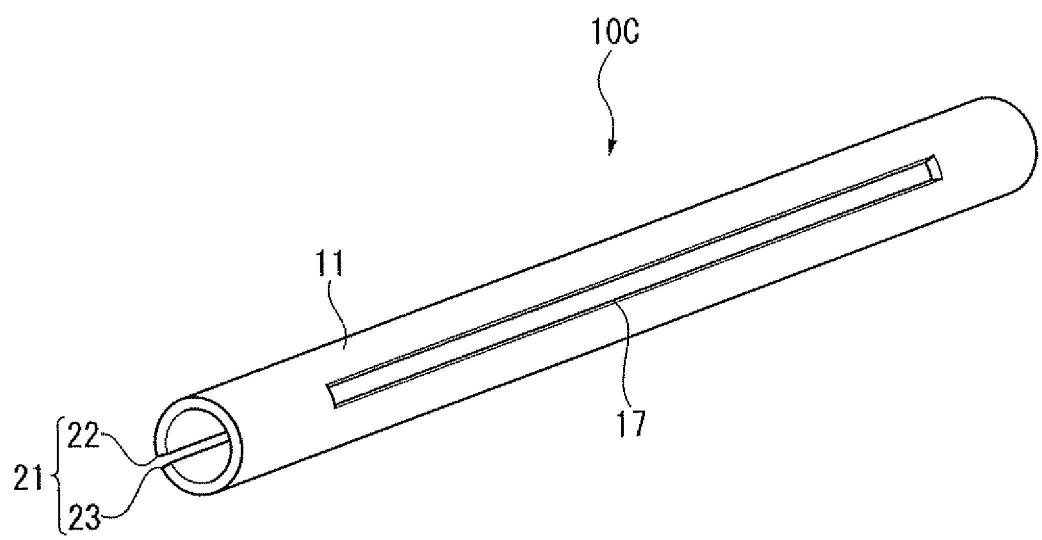
FIG. 13 is a perspective view showing the nail correcting device according to the third exemplary embodiment.

Third Exemplary Embodiment (See FIGS. 12 and 13)

As shown in FIG. 12, a nail correcting device 10C according to a third exemplary embodiment is different from the nail correcting device 10B according to the second exemplary embodiment in that a notched groove 17 is formed in the cylindrical body 11 at the opposite position of the slit 21 along the longitudinal direction of the cylindrical body 11 so that the distal end of the nail 1 projects from the notched groove 17.

As shown in FIG. 13, the notched groove 17 is formed along the longitudinal direction of the cylindrical body 11 and has a sufficient dimension for the distal end of the nail 1 to be inserted therein. Thus, since the distal end of the nail 1 can be inserted in the notched groove 17 of the nail correcting device 10C, the upper holder 22 and the lower holder 23 of the nail correcting device 10C can hold the nail 1 at a deep position toward the proximal end of the nail 1 relative to the distal end of the nail 1.

According to the third exemplary embodiment, the cylindrical body 11 of the nail correcting device 10C is provided with the notched groove 17 in which the distal end of the nail 1 is inserted. When the distal end of the nail 1 is inserted in the notched groove 17, the slit 21 can hold the nail 1 at a deep position toward the proximal end of the nail 1 relative to the distal end of the nail 1, so that an accidental detachment of the nail correcting device 10C from the nail 1 is unlikely to happen.

The above arrangement can also prevent the edges of the cylindrical body 11 at both ends thereof from, for instance, being caught by clothes or the like. Additionally, with the notched groove 17, it is not necessary to cut the nail 1 in a rectangle for attaching the nail correcting device 10C. The nail correcting device 10C is easily attachable to even a long nail.

Figure 14:
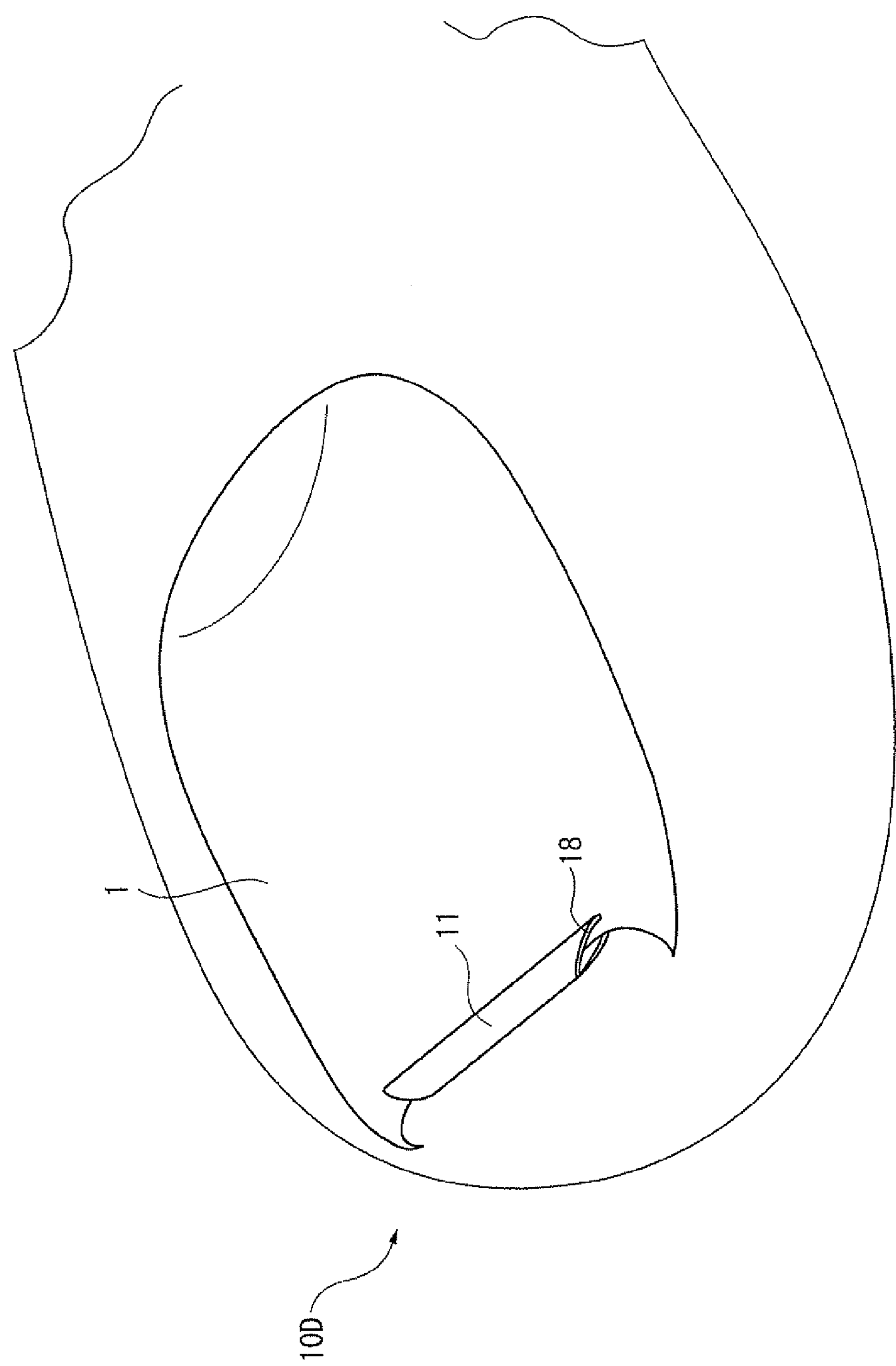
FIG. 14 is a perspective view showing a nail correcting device according to a fourth exemplary embodiment of the invention attached to a nail.
Figure 15:
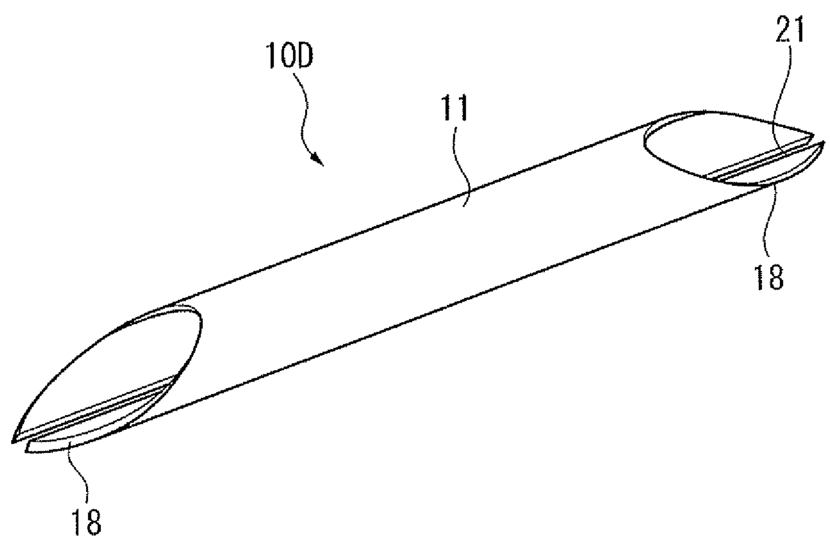
FIG. 15 is a perspective view showing the nail correcting device according to the fourth exemplary embodiment.

Fourth Exemplary Embodiment (See FIGS. 14 and 15)

As shown in FIG. 14, a nail correcting device 10D according to a fourth exemplary embodiment is different from the nail correcting device 10B according to the second exemplary embodiment in the shape of cut surfaces of the cylindrical body 11 at both ends thereof. Specifically, substantially oval cut surfaces 18 are formed in the cylindrical body 11 at both ends thereof.

As shown in FIG. 15, the nail correcting device 10D is attached to the nail 1 in such a manner that the substantially oval cut surfaces 18 are oriented outward. Specifically, each of the end portions of the cylindrical body 11 is cut in a substantially trapezoid in plan view such that a longitudinal direction defined on a side where the slit 21 is formed corresponds to the long side of the trapezoid while a longitudinal direction defined on the opposite side corresponds to the short side of the trapezoid.

According to the fourth exemplary embodiment, since the end portions of the cylindrical body 11 are cut, when the nail correcting device 10D is attached to the nail 1, the edges of the cylindrical body 11 at both ends thereof can be prevented from, for instance, being caught by clothes or the like.

Modifications (See FIGS. 16 to 24)

Although the best arrangement, method, and the like for carrying out the invention have been described above, the scope of the invention is not limited thereto. Thus, a shape, quantity and the like described above merely serve to exemplify the invention for facilitating an understanding of the invention, and do not serve as any limitations on the invention, so that what is described by a name of a component for which the description of the shape, quantity and the like are partially or totally omitted is also included in the invention.

Although a superelastic material is used to form the nail correcting devices 10A to 10D in the above exemplary embodiments, any other material may also be usable as long as the material has elasticity. For instance, a resin, a material having a shape-memory effect, and stainless steel may also be usable.

With the nail correcting device formed of a material having a shape-memory effect whose Af point (shape-recovery temperature) is a temperature slightly higher than the body temperature (e.g., 38 degrees C. or higher), although the nail correcting device usually exhibits a small correcting force, when the nail is softened during bath time or the like, the nail correcting device exhibits a large correcting force because the elastic modulus thereof approximately triples. When a strong pain from a deformed nail disturbs an ordinary life, the foot or the nail may be heated with hot water or a dryer to heat the correcting device to the Af point or higher. As a result, the correcting force can be increased, so that the nail is prevented from digging, thereby easing the pain in the foot.

Simultaneously, the correcting force is also increased due to the phase transformation of the material. For instance, in a relatively hot bath, while the nail is softened, the shape of the nail correcting device is recovered to correct the nail with a further increased correcting force. Thus, an enhanced correcting effect can be provided with less load on the nail.

Although the clearance dimension S of the slit 21 is constant in the longitudinal direction of the cylindrical body 11 in the exemplary embodiments, the clearance dimension may be varied in the longitudinal direction of the cylindrical body 11.

Specifically, the clearance dimension S may be gradually increased from the center of the cylindrical body 11 toward the ends of the cylindrical body 11 so that the nail 1 can be easily inserted in the nail correcting devices 10A to 10D. In contrast, the clearance dimension S of the slit 21 may be gradually narrowed from the center of the cylindrical body 11 toward the ends of the cylindrical body 11 so as to increase the correcting force on the nail to reduce the possibility of an accidental detachment of the nail correcting devices 10A to 10D from the nail 1. In other words, by changing the clearance dimension S of the slit 21 in accordance with the deformation of the nail 1 to be corrected, or the like, the nail correcting device is suitably usable for the nail 1.

Figure 16:
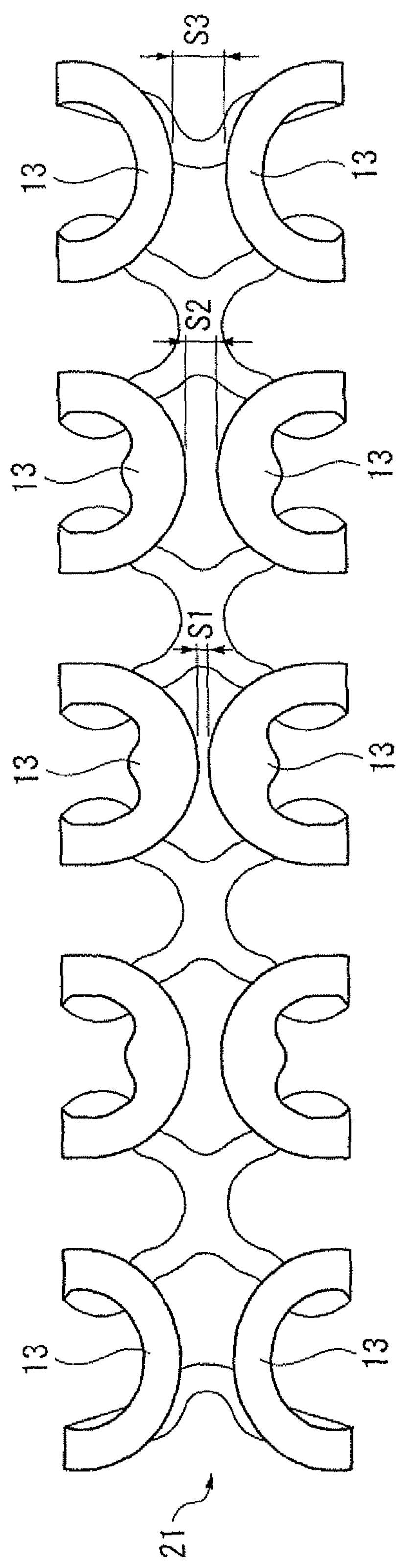
FIG. 16 shows a modification 1 in which a slit of the nail correcting device according to the first exemplary embodiment has a different clearance dimension.
Figure 17:
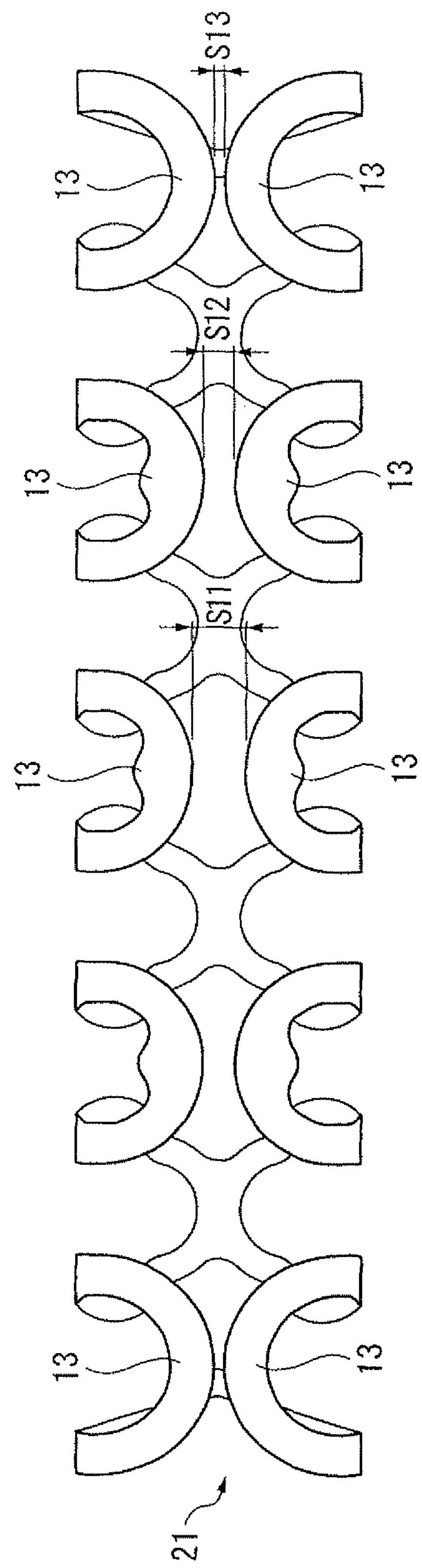
FIG. 17 shows a modification 2 in which the slit of the nail correcting device according to the first exemplary embodiment has a different clearance dimension.

For instance, in the first exemplary embodiment, as shown in FIG. 16, there may be provided a gradually increased clearance dimension, i.e., a clearance dimension S1 being defined between the holding teeth 13 on the center of the cylindrical body 11, a clearance dimension S2 being defined between the holding teeth 13 on a side closer to each end of the cylindrical body 11 and being larger than the clearance dimension S1, and a clearance dimension S3 being defined between the holding teeth 13 on a side further closer to each end of the cylindrical body 11 and being larger than the clearance dimension S2. With this arrangement, the nail 1 can be easily inserted in the nail correcting device 10A. In contrast, as shown in FIG. 17, there may be provided a gradually narrowed clearance dimension, i.e., a clearance dimension S11 being defined between the holding teeth 13 on the center of the cylindrical body 11, a clearance dimension S12 being defined between the holding teeth 13 on a side closer to each end of the cylindrical body 11 and being narrower than the clearance dimension S11, and a clearance dimension S13 being defined between the holding teeth 13 on a side further closer to each end of the cylindrical body 11 and being narrower than the clearance dimension S12. With this arrangement, the correcting force on the nail can be increased, so that an accidental detachment of the nail correcting device 10A from the nail 1 is unlikely to happen.

The respective shapes of the dividing grooves 12, the holding teeth 13 and the coupling piece 14, which are formed in the outer circumferential surface of the cylindrical body 11, may be different from those described above in the above exemplary embodiments.

Figure 18:
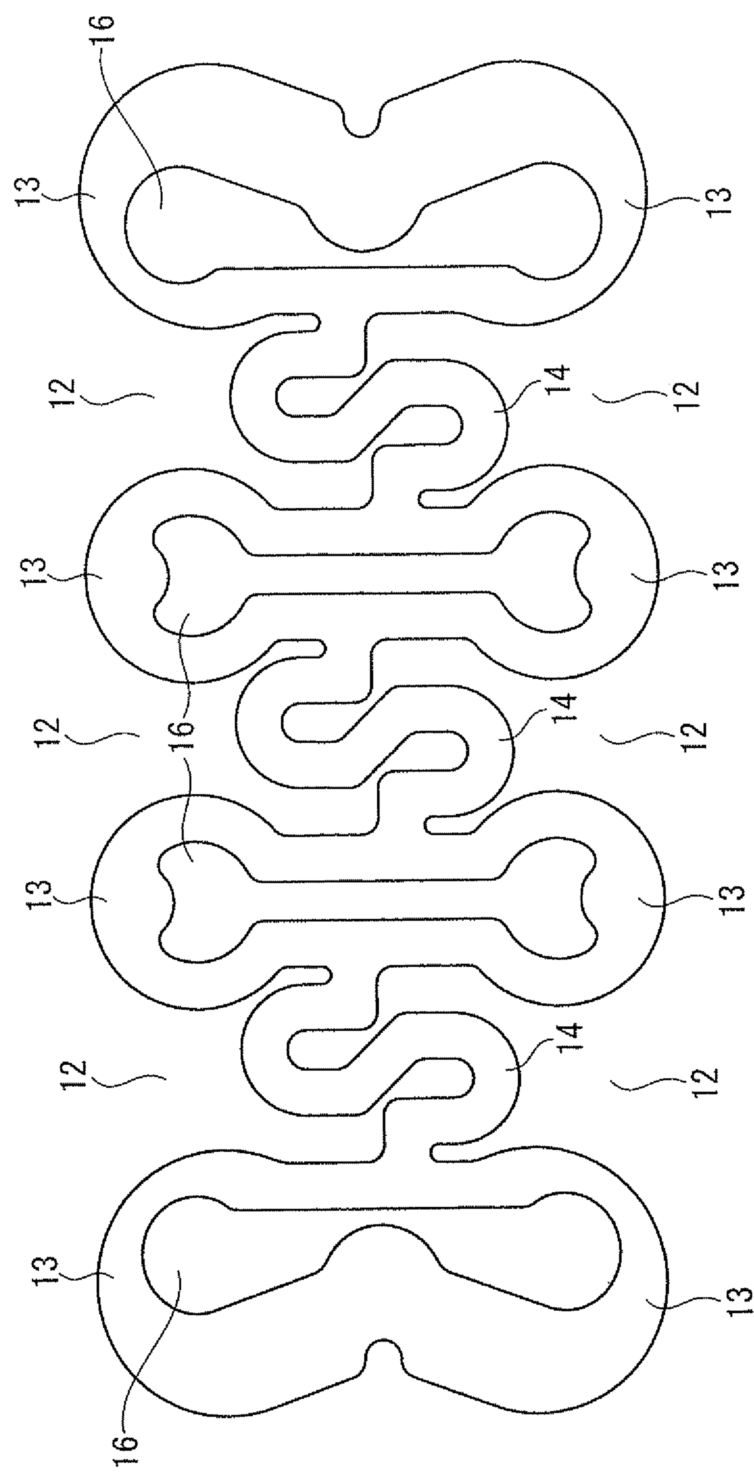
FIG. 18 is a developed view showing a different pattern of the nail correcting device according to the first exemplary embodiment.
Figure 19:
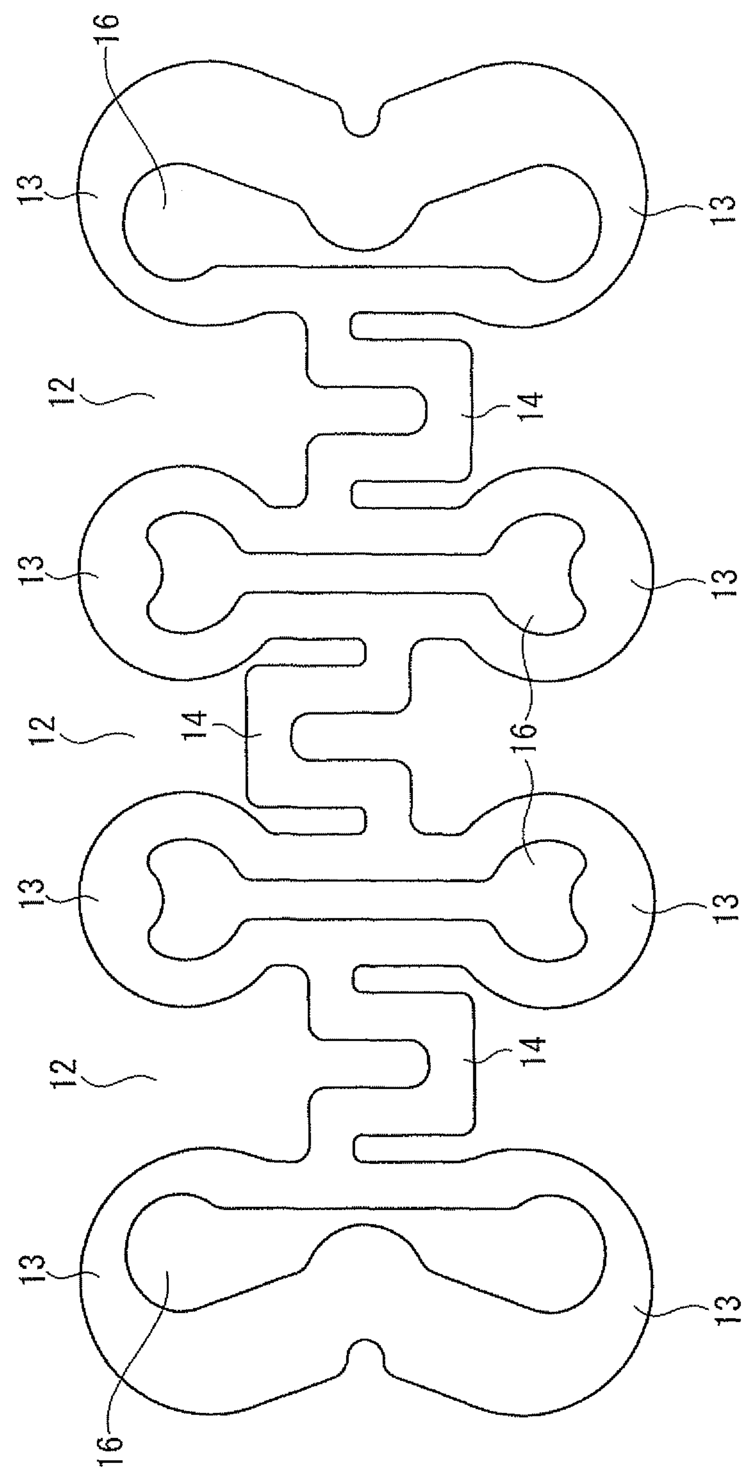
FIG. 19 is a developed view showing another different pattern of the nail correcting device according to the first exemplary embodiment.

For instance, each of the coupling pieces 14 may be formed in an S-shape as shown in a developed view of FIG. 18 (corresponding to FIG. 4), or may be formed in a U-shape or an inverse U-shape as shown in a developed view of FIG. 19 (corresponding to FIG. 4). With these arrangements, a curvature in an axial direction can be increased.

The spaces 16 of the nail correcting device shown in FIG. 18 and FIG. 19 are each shaped such that portions surrounded by the holding teeth 13 opposite to each other have the largest width and these portions are connected to each other via a portion having a parallel width.

Although it is described above that the holding teeth 13 have the same shape in the longitudinal direction of the cylindrical body 11, for instance, the widths of the holding teeth 13 formed on the ends of the cylindrical body may be wider than the widths of the holding teeth 13 formed around the center of the cylindrical body.

Although the dividing grooves 12, the holding teeth 13 and the coupling pieces 14 are formed in the outer circumferential surface of the cylindrical body 11 by laser process or etching process, these components may be formed in a different manner. For instance, a plate-like material may be cut to form the dividing grooves 12 and the spaces 16 by laser process or pressing process, and then may be formed in a cylindrical shape after the holding teeth 13 and the coupling pieces 14 are formed. Alternatively, a plastic molding process or the like may be used.

After the dividing grooves 12, the holding teeth 13 and the coupling pieces 14 are formed in the outer circumferential surface of the cylindrical body 11 by laser process, etching process, pressing process, plastic molding process or the like, the surfaces of these components may be polished or plated. Additionally, the surfaces may be colored or be provided with a design to enhance a decorative effect.

Although the holding teeth 13 of each pair formed in the cylindrical body 11 include the belt-like frame 15 formed with a substantially constant width in conformity with the outer profile, and the space 16 being surrounded by the belt-like frame 15 in the first exemplary embodiment, the holding teeth 13 are not limited thereto. For instance, the formation of the space 16 may be omitted.

Although it is described above that the end of each of the holding teeth 13 is in a semicircle or arc, the front end may be linearly formed. In other words, each of the holding teeth 13 may be formed in a rectangle, the corner of which may be rounded.

Although the cylindrical body 11 has a circular cross-sectional shape in the first exemplary embodiment, the cross-sectional shape may be a flattened circle or a polygon.

Figure 20:
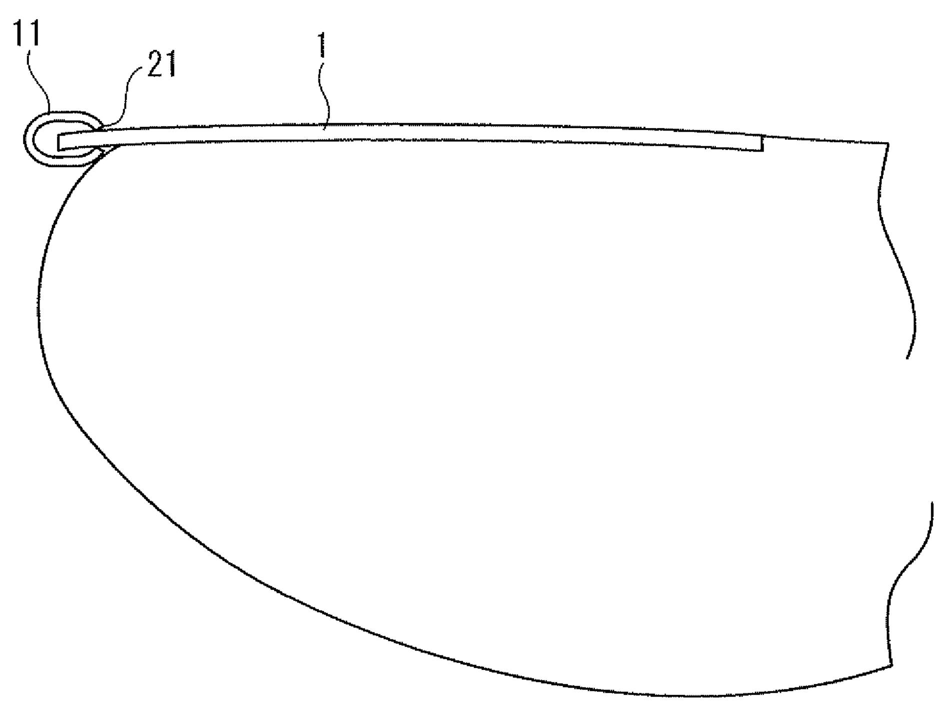
FIG. 20 shows a modification in which a cylindrical body of the nail correcting device according to any one of the above exemplary embodiments has an oval cross-sectional shape.

For instance, as shown in FIG. 20, it is preferable that the cylindrical body 11 has a cross-sectional shape in a flattened circle so that the dimension of the cylindrical body 11 in a thickness direction of the nail 1 is reduced when the nail correcting device is attached to the nail 1. With this arrangement, an unevenness between the upper surface of the nail and the upper surface of the nail correcting device is reduced, so that socks or the like can be easily put on or taken off without being caught by the nail correcting device.

Figure 21:
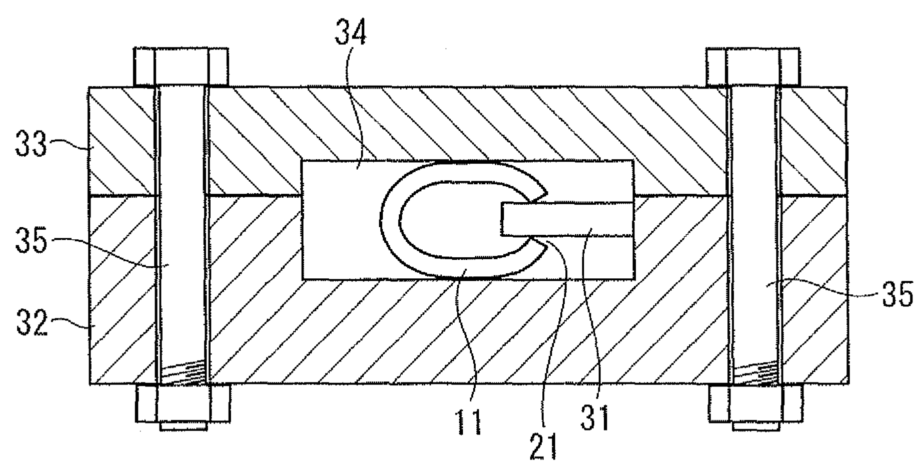
FIG. 21 shows a die for manufacturing the nail correcting device shown in FIG. 20.

For the above arrangement, as shown in FIG. 21, after inserting a spacer 31 in the slit 21 of the nail correcting device, the nail correcting device is set in a cavity 34 formed between a lower die 32 and an upper die 33 and then the lower die 32 and the upper die 33 are tightened with an attachment 35 such as bolt and nut. In this manner, the nail correcting device can be formed in a flattened cylindrical shape.

Although the cylindrical body 11 is provided with the five pairs of holding teeth 13 in the first exemplary embodiment, the number of the holding teeth 13 is not limited thereto. For instance, two, three, four, six or more pairs of holding teeth 13 may be provided.

Figure 22:
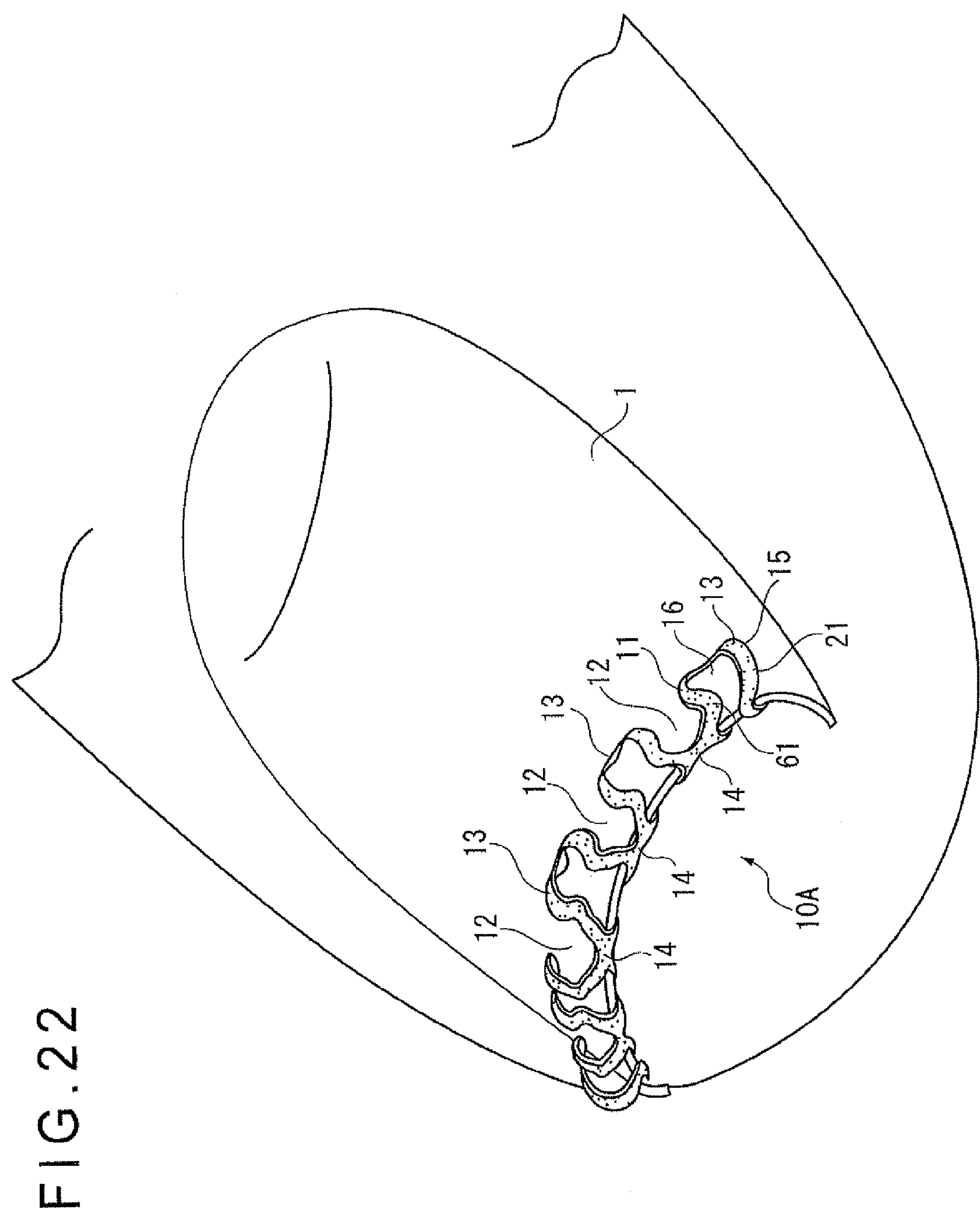
FIG. 22 shows a modification in which the nail correcting device according to the first exemplary embodiment is resin-coated.

In the first exemplary embodiment, as shown in FIG. 22, the entirety of the cylindrical body 11, i.e., the holding teeth 13 and the coupling pieces 14, may be coated with a resin 61, examples of which are resins such as polyurethane, silicone and vinyl chloride, and an ultraviolet curable resin. With this arrangement, even when the cylindrical body 11 is curved along the nail 1, the nail 1 can be prevented from being caught by the holding teeth 13. The cylindrical body 11 may be coated with a hydrophilic resin or a water-repellent resin.

The nail correcting device may be impregnated or coated with a medical agent in place of the resin 61. Examples of the medical agent include a therapeutic agent for fungal infection, an antibacterial agent capable of killing or deactivating germs for infection treatment, and the like. Examples of these agents are croconazole hydrochloride, butenafine hydrochloride, siccanin and tolnaftate.

With the above arrangement, since the nail correcting device is impregnated or coated with the medical agent, the medical agent can be applied to a soft tissue of the foot (e.g., a toe skin) for prophylaxis or treatment of fungal infection or the like.

Figure 23:
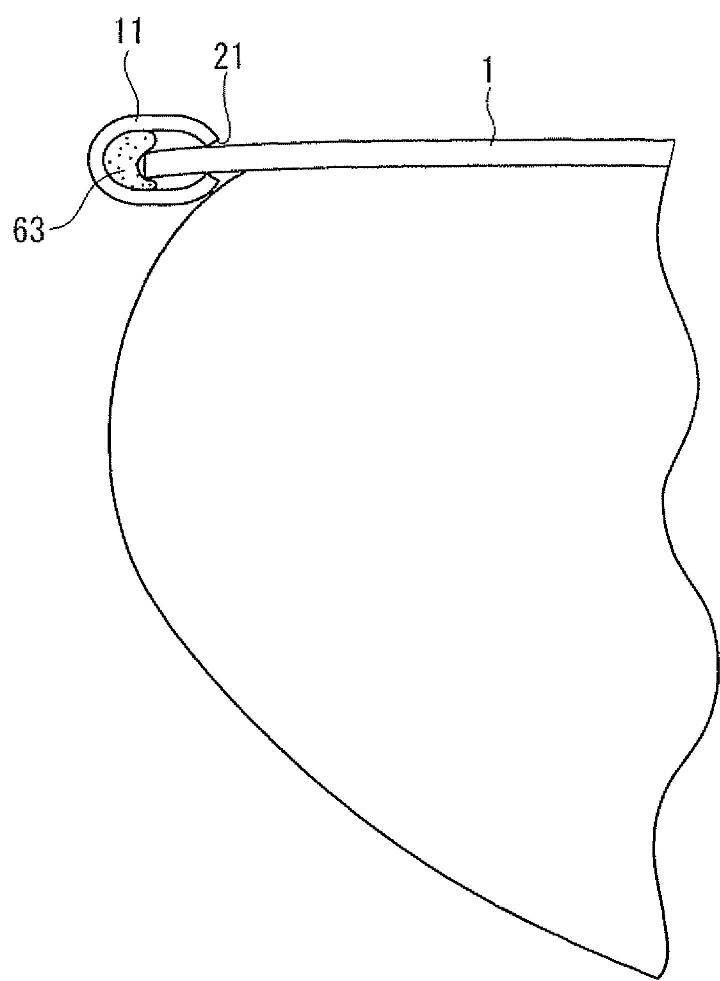
FIG. 23 shows a modification in which a medical capsule is housed in the cylindrical body of the nail correcting device according to any one of the above exemplary embodiments.

As shown in FIG. 23, a medical capsule 63 that contains a medical agent such as a therapeutic agent for fugal infection or an antibacterial agent may be housed inside the cylindrical body 11. The medical capsule 63 has a sufficient elasticity for gradually ejecting the contained medical agent.

With the above arrangement, the above treatment effect can be achieved simply by setting the medical capsule 63 in the cylindrical body 11.

Figure 24:
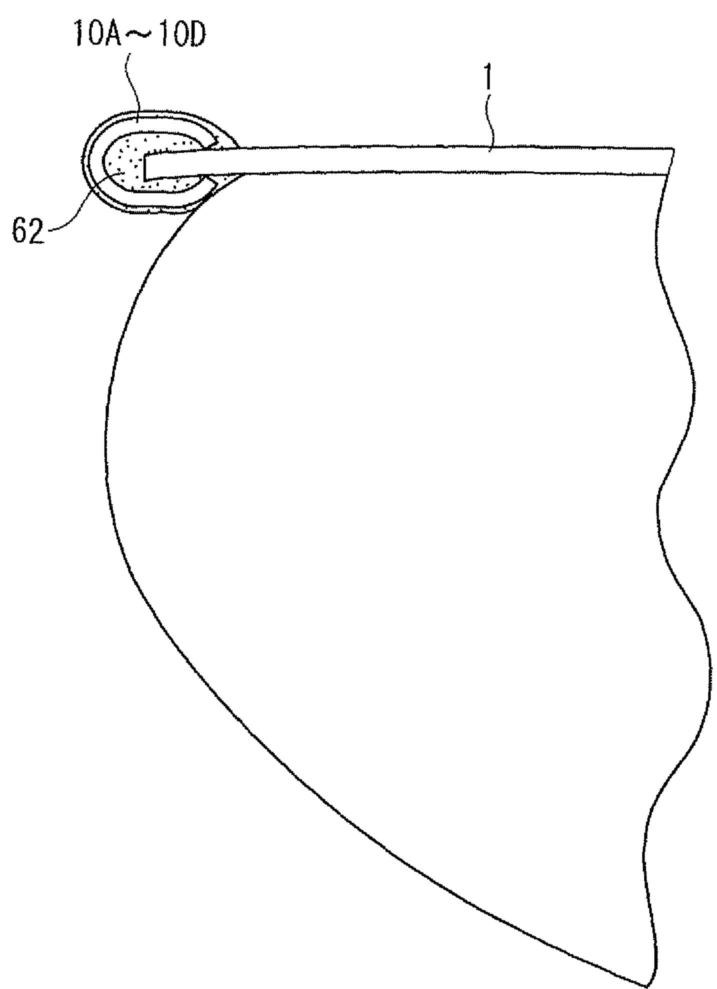
FIG. 24 shows a modification in which the nail correcting device according to the first exemplary embodiment is fixed with an adhesive.

As shown in FIG. 24, a medical set for nail correction may be provided by combining any one of the nail correcting devices 10A to 10D and an adhesive 62 usable to fix the one of the nail correcting devices 10A to 10D to the nail 1.

Generally, when the clearance of the slit formed in the cylindrical body is small, it is difficult to fit the nail correcting device to a nail. On the other hand, when the clearance of the slit is large, an accidental detachment of the nail correcting device from a nail is likely to happen. Accordingly, it is desired that the nail correcting device should solve such contradictory problems. However, nail thickness differs among people and among fingers to which the device is to be attached. While the nail of a thumb is thick, those of an index finger, a middle finger, ring finger and little finger are thin.

The arrangement shown in FIG. 24 includes the adhesive 62 usable to fix the one of the nail correcting devices 10A to 10D to the nail 1, so that after the one of the nail correcting devices 10A to 10D is attached to the nail 1, the adhesive 62 can be applied thereon to fix the one of the nail correcting devices 10A to 10D to the nail 1. Thus, even when the nail correcting devices 10A to 10D are formed to be easily attachable to the nail 1, an accidental detachment of the nail correcting devices 10A to 10D from the nail 1 is unlikely to happen.

For the adhesive 62, a topcoat (an aqueous acrylic), a gel nail polish (a gel resin curable by ultraviolet irradiation), and the like are usable.

It is further preferable that the adhesive 62 is impregnated with, for instance, a therapeutic agent for fugal infection, an antibacterial agent, or the like. When the nail correcting device is impregnated with the medical agent, the medical agent can be applied to a soft tissue of the foot (e.g., a toe skin) for prophylaxis or treatment of fungal infection or the like.

EXAMPLES

Figure 25:
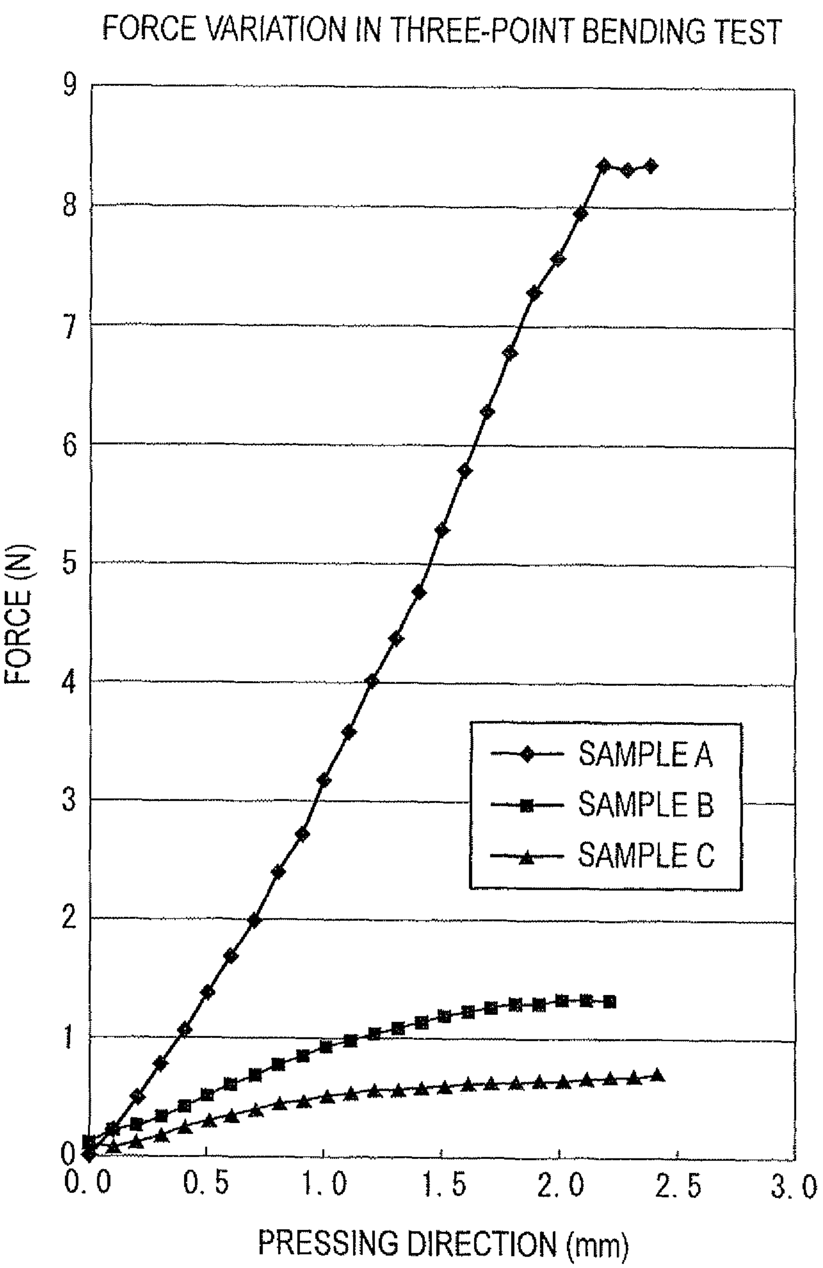
FIG. 25 shows a variation in force in a three-point bending test on the nail correcting device according to the first exemplary embodiment.

First Example (See FIG. 25)

Samples A, B and C of the nail correcting device 10A according to the first exemplary embodiment were manufactured. The sample A was formed of stainless steel and the clearance dimension S of the slit 21 thereof was 0.4 mm. The samples B and C were formed of a superelastic material (nitinol: nickel-titanium alloy) and the clearance dimensions S of the slits 21 thereof were 0.365 mm and 0.276 mm, respectively. A variation in a bending force for each of the samples A, B and C was measured.

According to a measurement method, both ends of the nail correcting device 10A were supported to measure a relationship between a pressing force required to press the center of the nail correcting device 10A downward by a pressing jig and a pressing distance (mm) at the center of the nail correcting device 10A (a three-point bending test).

Measurement results are shown in FIG. 25.

From the results, it has been found that each of the samples B and C exhibited a relatively gentle correcting force. It has been found that the sample A exhibited a large correcting force depending on the pressing distance (mm). In view of the above, when it is expected that application of a large correcting force at the initial stage of treatment gives a pain to a patient, the sample B or C is usable to correct an ingrown nail or the like with less pain given to the patient.

Second Example (See FIG. 26)

Samples of the nail correcting device 10A according to the first exemplary embodiment were formed of a superelastic material (nitinol). The outer diameter D and the longitudinal dimension L of the cylindrical body of each sample were 2 mm and 14 mm, respectively. The samples were different in the clearance dimension S of the slit 21, i.e., 0.7 mm, 0.8 mm, 0.9 mm, 1.0 mm and 1.1 mm. There were two types of samples prepared, i.e., samples whose surfaces were coated with a coating material, i.e., a topcoat (an aqueous acrylic), and samples without topcoat coating. A force required to pull each sample away from a nail was measured.

According to a measurement method, each of these samples of the nail correcting device was attached to an artificial nail made of phosphor bronze (distal end radius: 5 mm, thickness: 0.8 mm), and an unmating force required to pull the attached sample of the nail correcting device away was measured by a tension gauge.

Measurement results are shown in FIG. 26.

The results show that the samples whose surfaces were coated with a coating material required a large unmating force as compared with those without a coating material. In view of the above, it has been confirmed that the surface of the nail correcting device is preferably coated with a coating material so as to be easily detachable from a nail.

Figure 27:
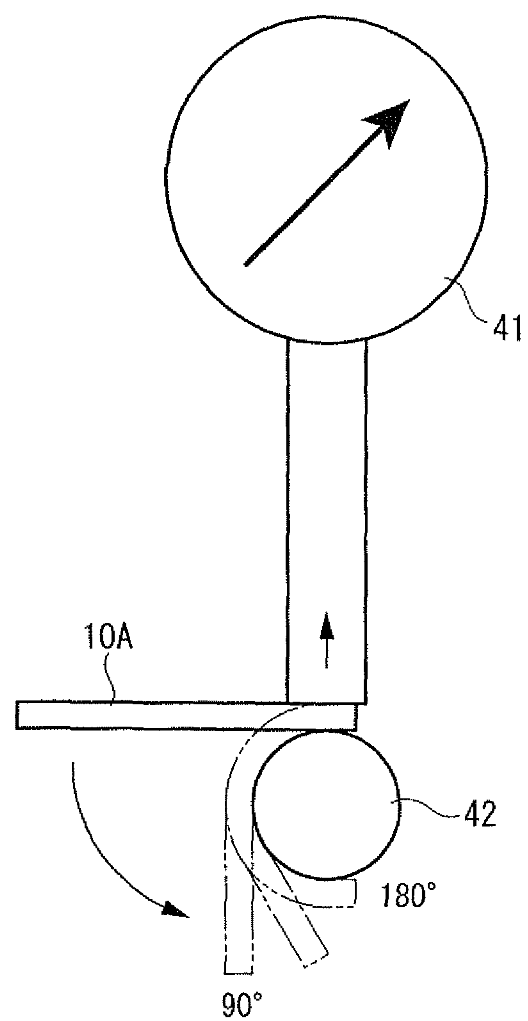
FIG. 27 shows a circular bending test on the nail correcting device according to the first exemplary embodiment.

Third Example (See FIGS. 27 and 28)

A sample of the nail correcting device 10A according to the first exemplary embodiment (five pairs of holding teeth) was formed of a superelastic material (nitinol). The outer diameter D and the longitudinal dimension L of the cylindrical body of the sample were 2.4 mm and 17 mm, respectively. The clearance dimension S of the slit 21 of the sample was 1.0 mm. As shown in FIG. 27, the sample was held at one end thereof by a force gauge 41 and was bent at the other end thereof around a plug 42 by 90 degrees, 120 degrees, 150 degrees and 180 degrees. A value of the force gauge 41 (a correcting force) and a deformation (loss of resilience) were checked in each bending (a circular bending test).

Measurement results are shown in FIG. 28.

From FIG. 28, it has been confirmed that the correcting force of the nail correcting device was not significantly changed depending on an increase in the bending angle of the nail correcting device.

What is claimed is:

1. A nail correcting device comprising:

a body formed of an elastic material and having an outer profile that is cylindrical; and a slit formed in a longitudinal direction of the body from one end to an opposite end of the body, the body further comprising:

an upper holder and a lower holder respectively provided at opposed faces of the slit, the upper holder and the lower holder each including plural pairs of holding teeth plurally divided in the longitudinal direction of the body by dividing grooves formed along a circumferential direction of the body, such that the holding teeth of each pair are opposed to each other across the slit to hold a distal end of a nail, and coupling pieces configured to couple adjacent pairs of the holding teeth on an opposite side of the slit, wherein the nail correcting device is adapted to be attached to the distal end of the nail inserted into the slit by only the upper and the lower holders.

2. The nail correcting device according to claim 1, wherein each pair of holding teeth comprises: a frame formed with a substantially constant width along an outer profile of the holding teeth; and a space surrounded by the frame.

3. The nail correcting device according to claim 2, wherein an end of each of the holding teeth is formed in an arc.

4. The nail correcting device according to claim 1, wherein an end of each of the holding teeth is formed in an arc.

5. The nail correcting device according to claim 1, wherein the nail correcting device is formed of a material exhibiting any one of a superelasticity effect and a shape-memory effect.

6. The nail correcting device according to claim 1, wherein the nail correcting device is coated or impregnated with a medical agent.

7. The nail correcting device according to claim 1, wherein a medical capsule is housed inside the cylindrical body, the medical capsule being configured to contain a medical agent and gradually eject the contained medical agent.

8. A medical set for nail correction, comprising:

the nail correcting device according to claim 1; and an adhesive used to fix the nail correcting device on a nail.

9. The medical set according to claim 8, wherein the adhesive is impregnated with a medical agent.

10. A nail correcting device comprising:

a cylindrical body formed of an elastic material; and a slit formed in a longitudinal direction of the cylindrical body from one end to an opposite end of the cylindrical body, the cylindrical body comprising:

an upper holder and a lower holder respectively provided at opposed faces of the slit, the upper holder and the lower holder each including plural pairs of holding teeth such that the holding teeth of the upper holder are opposed to the holding teeth of the lower holder across the slit, and coupling pieces configured to couple adjacent pairs of the holding teeth on an opposite side of the slit.

wherein the nail correcting device is adapted to be attached to a distal end of a nail inserted into the slit by only the holding teeth of the upper holder and the holding teeth of the lower holder.

11. The nail correcting device according to claim 1, wherein the nail correcting device is coated or impregnated with a medical agent.

12. The nail correcting device according to claim 1, wherein a medical capsule is housed inside the cylindrical body, the medical capsule being configured to contain a medical agent and gradually eject the contained medical agent.

13. A nail correcting device comprising:

a cylindrical body formed of an elastic material; and a slit formed in a longitudinal direction of the cylindrical body from one end to an opposite end of the cylindrical body, the cylindrical body comprising an upper holder and a lower holder respectively provided at opposed faces of the slit, wherein the upper holder and the lower holder each include plural pairs of holding teeth, the holding teeth of the upper holder being opposed to the holding teeth of the lower holder across the slit, wherein the nail correcting device is adapted to be attached to a distal end of a nail inserted into the slit by only the holding teeth of the upper holder and the holding teeth of the lower holder; and coupling pieces configured to couple adjacent pairs of the holding teeth on an opposite side of the slit.

* * * * *